United States Patent
Oliva

(10) Patent No.: US 9,987,301 B2
(45) Date of Patent: *Jun. 5, 2018

(54) HEPARIN-BASED COMPOSITIONS AND METHODS FOR THE INHIBITION OF METASTASIS

(71) Applicant: Eugene J. Oliva, Emerson, NJ (US)

(72) Inventor: Eugene J. Oliva, Emerson, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/930,319

(22) Filed: Nov. 2, 2015

(65) Prior Publication Data

US 2016/0051575 A1   Feb. 25, 2016

Related U.S. Application Data

(60) Continuation of application No. 14/564,967, filed on Dec. 9, 2014, now Pat. No. 9,173,889, which is a division of application No. 13/477,012, filed on May 21, 2012, now Pat. No. 8,912,167.

(60) Provisional application No. 61/511,244, filed on Jul. 25, 2011, provisional application No. 61/488,068, filed on May 19, 2011.

(51) Int. Cl.
*A61K 31/167*  (2006.01)
*A61K 31/727*  (2006.01)
*A61K 45/06*   (2006.01)
*A61K 9/00*    (2006.01)
*A61K 31/609*  (2006.01)

(52) U.S. Cl.
CPC .......... *A61K 31/727* (2013.01); *A61K 9/0019* (2013.01); *A61K 31/167* (2013.01); *A61K 31/609* (2013.01); *A61K 45/06* (2013.01)

(58) Field of Classification Search
None
See application file for complete search history.

(56) References Cited

PUBLICATIONS

Nakamura, Journal of Biomedical Materials Research Part A, Dec. 2009; 91(3): 814-23.*

* cited by examiner

*Primary Examiner* — Layla D Berry

(57) ABSTRACT

The invention provides the use in combination of a heparin containing composition that has anticoagulant activity when used alone, such as an unfractionated heparin or low molecular weight heparin, in combination with an inhibitor of the anticoagulation activity/effect or effect of heparin, for the inhibition of metastasis.

9 Claims, No Drawings

HEPARIN-BASED COMPOSITIONS AND METHODS FOR THE INHIBITION OF METASTASIS

CROSS-REFERENCE TO RELATED APPLICATIONS

This application is a continuation of U.S. application Ser. No. 14/564,967 filed Dec. 9, 2014 (now U.S. Pat. No. 9,173,889) which is a division of U.S. application Ser. No. 13/477,012 filed May 21, 2012 (now U.S. Pat. No. 8,912,167) which claims the benefit of U.S. provisional patent application Ser. Nos. 61/511,244 filed Jul. 25, 2011 and 61/488,068 filed May 19, 2011, each of which is incorporated by reference in its entirety.

FIELD OF THE INVENTION

The invention relates to field of pharmaceutical prevention and treatment of metastasis.

BACKGROUND

Heparin is a mixture of glycosaminoglycan chains generally ranging in molecular weight from approximately 3,000 to 30,000 Daltons. Both unfractionated and low molecular weight heparins are utilized in medicine for their anticoagulant activity. Many studies have also now documented that unfractionated and low molecular weight heparins inhibit cancer cell metastasis. However, the use of heparins in the prevention or treatment of cancer metastasis is severely limited by the anticoagulant activity.

What is needed and provided by the present invention are compositions and related methods that permit the anti-metastatic activity of heparin to be used in the treatment of cancer by reducing or eliminating the anticoagulant activity of heparin.

SUMMARY OF THE INVENTION

One embodiment of the invention provides a pharmaceutical composition for the inhibition of metastasis that includes:
 an anti-metastatic heparin preparation having anti-coagulant activity in the absence of an inhibitor thereof; and
 an inhibitor of the anti-coagulation activity of heparin or a pharmaceutically-acceptable salt thereof.

The composition may be dry or friable. The composition may further comprise water and be a liquid. If the composition is dry, it may be reconstitutable with water or aqueous solution to a liquid form suitable for intravenous administration or injection such as subcutaneous or bolus injection in a mammal such as a human. The heparin preparation may be present in the composition in an amount effective to inhibit metastasis and the inhibitor of the anti-coagulation activity of heparin in the composition may be present in an amount effective to at least partially inhibit, such as at least substantially inhibit, the anti-coagulation activity of the heparin preparation in the composition. At least a portion of the inhibitor of the anti-coagulation activity of heparin or a pharmaceutically-acceptable salt thereof in the composition may be bound to the heparin of the heparin preparation in the composition.

A related embodiment of the invention provides a method for preparing an aqueous pharmaceutical composition for the inhibition of metastasis in a mammal that includes mixing
 an anti-metastatic heparin preparation having anti-coagulant activity in the absence of an inhibitor thereof;
 an inhibitor of the anti-coagulation activity of heparin or a pharmaceutically-acceptable salt thereof; and
 water or an aqueous solution to obtain the aqueous pharmaceutical composition. The inhibitor may be a heparin-binding compound and the method may optionally include a further step of removing inhibitor that remains unbound to the heparin, for example, by filtering.

Another embodiment of the invention provides a pharmaceutical kit for the inhibition of metastasis that includes:
 an anti-metastatic heparin preparation having anti-coagulant activity in the absence of an inhibitor thereof; and
 an inhibitor of the anti-coagulation activity of or a pharmaceutically-acceptable salt thereof,
wherein, the heparin preparation is not mixed with the inhibitor of the anti-coagulation activity of heparin in the kit. The components may, for example, be provided in separate vials or other containers. Each of said components may be in dry form in the kit. The heparin preparation in the kit may be provided in an amount effective to inhibit metastasis and the inhibitor of the anti-coagulation activity of heparin in the kit may be provided in an amount effective to at least partially inhibit, such as at least substantially inhibit, the anti-coagulation activity of the heparin preparation in the kit.

A further embodiment of the invention provides a method for inhibiting metastasis in a mammal, that includes the step of:
 administering to a mammalian subject, such as a human, in need of inhibition of metastasis, an effective amount of a pharmaceutical composition that includes (i) an anti-metastatic heparin preparation having anti-coagulant activity in the absence of an inhibitor thereof, and (ii) an inhibitor of the anti-coagulation effect of heparin or a pharmaceutically-acceptable salt thereof. The mammalian subject may not be in need of treatment for pathological coagulation or not be in need of anti-coagulation generally. The subject may have a cancer that is susceptible to or exhibiting metastasis. The composition administered may contain an amount of the heparin preparation effective to inhibit metastasis and an amount of the inhibitor of the anti-coagulation activity of heparin effective to at least partially, for example, at least substantially, inhibit the anti-coagulation activity of the heparin preparation (while both components are in the body). Administration may, for example, include intravenous administration or injection, such as subcutaneous or intramuscular bolus injection.

Another embodiment of the invention provides a method for inhibiting metastasis in a mammal that includes the step of:
 administering, for example co-administering, to a mammalian subject in need of inhibition of metastasis,
  (i) an anti-metastatic heparin preparation having anticoagulant activity in the absence of an inhibitor thereof; and
  (ii) an inhibitor of the anti-coagulation effect of heparin or a pharmaceutically-acceptable salt thereof,
 such that the presence of the heparin preparation and the inhibitor in the mammalian subject are temporally overlapping. The mammalian subject may not be in need of treatment for pathological coagulation or not be in need of anti-coagulation generally. The heparin preparation may be administered in an amount effective to inhibit metastasis and the inhibitor of the anti-coagulation activity of heparin may be administered in an amount effective to at least partially, for example, at least substantially, inhibit the anti-coagulation activity of the heparin preparation (while both components are in the body). The subject may have a cancer that is susceptible to or exhibiting metastasis. Administration may, for example, include intravenous administration or injection, such as subcutaneous or intramuscular bolus injection.

A further embodiment of the invention provides the use in combination of an anti-metastatic heparin preparation having anti-coagulant activity in the absence of an inhibitor thereof and an inhibitor of the anti-coagulation activity of heparin for the inhibition of metastasis in a mammalian subject such as a human.

Another embodiment of the invention provides the use of a pharmaceutical composition including an anti-metastatic heparin preparation having anti-coagulant activity in the absence of an inhibitor thereof and an inhibitor of the anti-coagulation activity of heparin, for the inhibition of metastasis in a mammalian subject such as a human.

A further embodiment of the invention provides the use of an anti-metastatic heparin preparation having anti-coagulant activity in the absence of an inhibitor thereof and an inhibitor of the anti-coagulation activity of heparin for the preparation of a medicament for the inhibition of metastasis in a mammalian subject such as a human.

The heparin preparation in any of the aforementioned embodiments may include or be an unfractionated heparin preparation or a low molecular weight heparin preparation. The low molecular weight heparin preparation may, for example, include or be a heparin preparation selected from the group consisting of Tinzaparin, Reviparin and Enoxaparin.

The inhibitor of the anti-coagulation activity of heparin or a pharmaceutically-acceptable salt thereof may, for example, be any of the anti-heparin compounds disclosed herein including the specific compounds and compounds of the formulas disclosed herein (or their pharmaceutically acceptable salts). The inhibitor may, for example, be an inhibitor that binds heparin, such as binding an antithrombin binding site of heparin. In any of the aforementioned embodiments, the inhibitor of the anti-coagulation activity of heparin may include or be tetra-[5-(L)-lysyl-amino-O-methylsalicylamide] or a pharmaceutically-acceptable salt thereof.

Other objects and advantages of the invention will become apparent from the following description.

DETAILED DESCRIPTION OF THE INVENTION

The invention provides the use in combination of a heparin-containing composition that has anticoagulant activity when used alone, such as an unfractionated heparin or low molecular weight heparin, in combination with an inhibitor of the anticoagulation activity/effect or effect of heparin (or procoagulant generally), for the inhibition of metastasis. The heparin and inhibitor of the anticoagulation activity/effect of heparin may be provided in the same pharmaceutical composition or may be provided separately, but administered to the patient such that their effect is overlapping in the patient. The heparin component of the combination treatment inhibits metastasis while the inhibitor of the anticoagulation activity/effect of heparin ensures that the patient who is not in need of anticoagulation and/or may be harmed by anticoagulation, will at least partially, for example at least substantially, not have coagulation inhibited by the administered heparin.

The patient may, for example, be a patient diagnosed or previously diagnosed with a cancer that is known to metastasize (susceptible to metastasis) or a patient suspected of having or developing such a cancer. The amount of the heparin administered to the patient is effective to inhibit metastasis and the amount of the inhibitor of the anticoagulation activity/effect of heparin administered to the patient is effective to at least partially, for example at least substantially, inhibit the anticoagulation activity/effect of the administered heparin, for example, by at least 40%, by at least 50%, by at least 60%, by at least 70%, by at least 75%, by at least 80%, by at least 85% by at least 90%, or by at least 95%. The patient may be a mammal, such as a human patient. The primary cancer type may, for example, be lung cancer, NSCLC, breast cancer, ovarian cancer, prostate cancer, testicular cancer, pancreatic cancer, melanoma, sarcoma, cervical cancer, kidney (renal) cancer, gastric cancer, colon cancer, bladder cancer, mouth cancer, or throat cancer. The invention also provides methods for treating cancers with the compositions of the invention that are not conventionally thought of as metastatic or at risk of metastases but whose growth and spreading at one or more stages of disease may utilize some of the same biological interactions found in metastasis. Such cancers include myeloma such as multiple myeloma, leukemia, lymphoma, brain cancer and esophageal cancer.

Without limitation, various embodiments of the invention include:

1. A pharmaceutical composition for the inhibition of metastasis, including: a heparin preparation; and an inhibitor of the anti-coagulation effect of heparin.

The composition may be a friable and/or dry admixture of the heparin preparation and the inhibitor of the anti-coagulation effect of heparin, which can be reconstituted with water or aqueous solution such as saline for intravenous administration or injection such as subcutaneous injection, to a mammalian patient/subject such as a human. Pharmaceutically acceptable excipients, such as but not limited to one or more carriers, may also be included in the composition. The composition may be a liquid preparation. Thus, it may further include water or aqueous solution in which the heparin preparation and inhibitor of the anti-coagulation effect of heparin are dissolved, suspended and/or dispersed. The liquid composition may be obtained by a method of reconstitution including a step of mixing the friable or dry mixture of the heparin preparation and inhibitor of the anti-coagulation effect of heparin with water such as with an aqueous solution such as saline. Alternatively, the liquid composition for administration may be prepared by sequentially mixing each the heparin preparation and inhibitor of the anti-coagulation effect of heparin and the water or aqueous in any manner, such as but not limited to adding one of the heparin preparation and inhibitor of the anti-coagulation effect of heparin to the water or aqueous solution and then the other component.

The inhibitor of the anti-coagulation effect of heparin may, for example, be a heparin-binding compound, such as one binding the antithrombin binding site of heparin and/or structurally mimicking the heparin binding site of antithrombin. At least a substantial quantity, such as at least 50%, at least 60%, at least 70%, at least 80%, at least 90%, at least 95% and at least 98% of the inhibitor of the anti-coagulation effect of heparin in the composition (dry or liquid) may, for example, be bound to the heparin in the composition, such as to the antithrombin site of the heparin. To manufacture a "dry" or friable composition in which the heparin and the heparin binding inhibitor are prebound, the components can be mixed together in water or an aqueous solution (for example, around a neutral pH) to permit such binding and then dried such as by lyophilization. Those skilled in the art will recognized that such a dry composition may still include some water and use of the term "dry" herein is not intended to suggest that no water molecules are present in a dry composition. The heparin and heparin binding inhibitor may also simply be admixed in a dry or friable composition so that the binding of the components does not substantially occur until they are mixed with water or aqueous solution.

2. The composition of embodiment 1, wherein the heparin preparation is present in an amount effective to inhibit metastasis and the inhibitor of the anti-coagulation activity of heparin is present in an amount effect to at least partially inhibit the anti-coagulation activity of the heparin preparation.

3. The composition of any one of the preceding embodiments, further including at least one pharmaceutically acceptable excipient.

4. The composition of any one of the preceding embodiments, wherein the heparin preparation is unfractionated heparin.

5. The composition of any one of the preceding embodiments, wherein the heparin preparation is a low molecular weight heparin.

6. The composition of embodiment 5, wherein the low molecular weight heparin is Tinzaparin, Reviparin, or Enoxaparin.

7. The composition of any one preceding embodiments wherein the inhibitor of the anti-coagulation effect of heparin includes a compound or a pharmaceutically-acceptable salt thereof, the compound being selected from the group consisting of: PMX-60056 (tetra-[5-(L)-lysyl-amino-O-methylsalicylamide], Polymedix; Kuziej et al., Clin Appl Thromb Hemost, 2010 August; 16(4):377-86); PMX-60102 (Polymedix); PMX-60126 (Polymedix); PMX-60138 (Polymedix); PMX-60100 (Polymedix); a salicylamide derivative; a compound disclosed in US Pub. No. 2009/0239811; protamine; a derivative of protamine; a peptide inhibitor of the anticoagulant activity of heparin such as one of those disclosed in Schick et al., Thromb Haemost, 2001 March 85(3):482-487; a peptide inhibitor disclosed in U.S. Pat. No. 6,855,801 or 7,259,140; and an fXa protein derivative such as one disclosed in US Pub. No. 2010/0125052.

8. A pharmaceutical kit for the inhibition of metastasis, including: a heparin preparation; and an inhibitor of the anti-coagulation effect of heparin.

9. The kit of embodiment 8, wherein the heparin preparation is provided in an amount effective to inhibit metastasis and the inhibitor of the anti-coagulation activity of heparin is provided in an amount effect to at least partially inhibit the anti-coagulation activity of the heparin preparation.

10. The kit of embodiment 8 or 9, wherein at least one of the heparin preparation and the inhibitor is provided mixed with at least one pharmaceutically acceptable excipient.

11. The kit of any one of embodiments 8-10, wherein the heparin preparation is an unfractionated heparin.

12. The kit of any one of embodiments 8-10, wherein the heparin preparation is a low molecular weight heparin.

13. The kit of embodiment 12, wherein the low molecular weight heparin is Tinzaparin, Reviparin, or Enoxaparin.

14. The kit of any one preceding embodiments wherein the inhibitor of the anti-coagulation effect of heparin includes a compound or a pharmaceutically-acceptable salt thereof, the compound being selected from the group consisting of: PMX-60056 (tetra-[5-(L)-lysyl-amino-O-methylsalicylamide], Polymedix; Kuziej et al., Clin Appl Thromb Hemost, 2010 August; 16(4):377-86); PMX-60102 (Polymedix); PMX-60126 (Polymedix); PMX-60138 (Polymedix); PMX-60100 (Polymedix); a salicylamide derivative; a compound disclosed in US Pub. No. 2009/0239811; protamine; a derivative of protamine; a peptide inhibitor of the anticoagulant activity of heparin such as one of those disclosed in Schick et al., Thromb Haemost, 2001 March 85(3):482-487; a peptide inhibitor disclosed in U.S. Pat. No. 6,855,801 or 7,259,140; and an fXa protein derivative such as one disclosed in US Pub. No. 2010/0125052.

15. A method for inhibiting metastasis in a mammal, including the step of:
    administering to a mammalian subject in need thereof, an effective amount of a pharmaceutical composition according to any one of embodiments 1-7.

The mammalian subject may be a non-human mammal or a human. The mammalian subject, such as a human, may be in need of inhibition or prevention of metastasis and not in need of anti-coagulation such as not in need of the anti-coagulation effect of heparin. Thus, the mammalian subject may be one that is not suffering from pathological coagulation activity. The mammalian subject, such as a human, may have or be suspected of having a cancer that is known to metastasize (susceptible to metastasizing) or is metastasizing, such as those described herein.

16. The method of embodiment 15, wherein the mammalian subject is a human patient.

17. A method for inhibiting metastasis in a mammal, including the step of:
    administering to a mammalian subject in need thereof,
    (i) a heparin preparation; and
    (ii) an inhibitor of the anti-coagulation effect of heparin, such that the presence of the heparin preparation and the inhibitor in the mammalian subject are temporally overlapping.

The mammalian subject may be a non-human mammal or a human. The mammalian subject, such as a human, may be in need of inhibition or prevention of metastasis and not in need of anti-coagulation such as not in need of the anti-coagulation effect of heparin. Thus, the mammalian subject may be one that is not suffering from pathological coagulation activity. The mammalian subject, such as a human, may have or be suspected of having a cancer that is known to metastasize (susceptible to metastasizing) or is metastasizing, such as those described herein.

18. The method of embodiment 17, wherein the heparin preparation and the inhibitor of the anti-coagulation activity of heparin are co-administered.

19. The method of embodiment 17 or 18, wherein the heparin preparation is administered in an amount effective to inhibit metastasis and the inhibitor of the anti-coagulation activity of heparin is administered in an amount effect to at least partially inhibit the anti-coagulation activity (or effect) of the heparin preparation.

20. The method of any one of embodiment 17 or 18, wherein the heparin preparation is an unfractionated heparin.

21. The method of any one of embodiments 17-19, wherein the heparin preparation is a low molecular weight heparin.

22. The method of embodiment 21, wherein the low molecular weight heparin is Tinzaparin, Reviparin, or Enoxaparin.

23. The method of any one of embodiments 17-22, wherein the inhibitor of the anti-coagulation effect of heparin is a compound or a pharmaceutically-acceptable salt thereof, the compound being selected from the group consisting of: PMX-60056 (tetra-[5-(L)-lysyl-amino-O-methyl-salicylamide], Polymedix; Kuziej et al., Clin Appl Thromb Hemost, 2010 August; 16(4):377-86); PMX-60102 (Polymedix); PMX-60126 (Polymedix); PMX-60138 (Polymedix); PMX-60100 (Polymedix); a salicylamide derivative; a compound disclosed in US Pub. No. 2009/0239811; protamine; a derivative of protamine; a peptide inhibitor of the anticoagulant activity of heparin such as one of those disclosed in Schick et al., Thromb Haemost, 2001 March 85(3):482-487; a peptide inhibitor disclosed in U.S. Pat. No. 6,855,801 or 7,259,140; and an fXa protein derivative such as one disclosed in U.S. Pub. No. 2010/0125052.

24. Use in combination of a heparin preparation and an inhibitor of the anti-coagulation activity of heparin for the inhibition of metastasis in a mammalian subject.

25. The use of embodiment 24, wherein the heparin preparation is an unfractionated heparin.

26. The use of embodiment 25, wherein the heparin preparation is a low molecular weight heparin.

27. The use of embodiment 26, wherein the low molecular weight heparin is Tinzaparin, Reviparin, or Enoxaparin.

28. The use of any one of embodiments 24-27, wherein the inhibitor of the anti-coagulation effect of heparin is a compound or a pharmaceutically-acceptable salt thereof, the compound being selected from the group consisting of: PMX-60056 (tetra-[5-(L)-lysyl-amino-O-methylsalicylamide], Polymedix; Kuziej et al., Clin Appl Thromb Hemost, 2010 August; 16(4):377-86); PMX-60102 (Polymedix); PMX-60126 (Polymedix); PMX-60138 (Polymedix); PMX-60100 (Polymedix); a salicylamide derivative; a compound disclosed in U.S. Pub. No. 2009/0239811; protamine; a derivative of protamine; a peptide inhibitor of the anticoagulant activity of heparin such as one of those disclosed in Schick et al., Thromb Haemost, 2001 March 85(3):482-487; a peptide inhibitor disclosed in U.S. Pat. No. 6,855,801 or 7,259,140; and an fXa protein derivative such as one disclosed in US Pub. No. 2010/0125052.

29. Use of a pharmaceutical composition according to any one of embodiments 1-7 for the inhibition of metastasis in a mammalian subject such as a non-human mammal or a human.

30. Use of a heparin preparation and an inhibitor of the anti-coagulation activity of heparin for the preparation of a medicament for the inhibition of metastasis in a mammalian subject such as a non-human mammal or a human.

31. The use of embodiment 30 wherein the heparin preparation is an unfractionated heparin.

32. The use of embodiment 30, wherein the heparin preparation is a low molecular weight heparin.

33. The use of embodiment 32, wherein the low molecular weight heparin is Tinzaparin, Reviparin, or Enoxaparin.

34. The use of any one of embodiments 30-33, wherein the inhibitor of the anti-coagulation effect of heparin is a compound or a pharmaceutically-acceptable salt thereof, the compound being selected from the group consisting of: PMX-60056 (tetra-[5-(L)-lysyl-amino-O-methylsalicylamide], Polymedix; Kuziej et al., Clin Appl Thromb Hemost, 2010 August; 16(4):377-86); PMX-60102 (Polymedix); PMX-60126 (Polymedix); PMX-60138 (Polymedix); PMX-60100 (Polymedix); a salicylamide derivative; a compound disclosed in U.S. Pub. No. 2009/0239811; protamine; a derivative of protamine; a peptide inhibitor of the anticoagulant activity of heparin such as one of those disclosed in Schick et al., Thromb Haemost, 2001 March 85(3):482-487; a peptide inhibitor disclosed in U.S. Pat. No. 6,855,801 or 7,259,140; and an fXa protein derivative such as one disclosed in U.S. Pub. No. 2010/0125052.

35. Any one of the preceding embodiments, wherein the inhibitor of the anti-coagulation effect of heparin is a heparin-binding compound, such as one binding the antithrombin binding site of heparin.

36. Any one of the preceding embodiments, wherein the inhibitor of the anti-coagulation effect of heparin is an anti-heparin compound of a formula disclosed in U.S. Publication No. 2011/0178104 A1 (U.S. application Ser. No. 12/984,634) or a specific compound disclosed therein, or a pharmaceutically acceptable salt of the compound(s).

37. Any one of the preceding embodiments, wherein the inhibitor of the anti-coagulation effect of heparin is tetra-[5-(L)-lysyl-amino-O-methylsalicylamide] (PMX-60056) or a pharmaceutically acceptable salt thereof.

A further embodiment of the invention provides a method for treating a cancer susceptible to metastasis in a mammal, that includes the step of:

administering to a mammalian subject, such as a human, having/diagnosed with a cancer susceptible to metastasis (such as those described herein), for example, not yet or already metastasizing, an effective amount of a pharmaceutical composition that includes (i) an anti-metastatic heparin preparation having anti-coagulant activity in the absence of an inhibitor thereof, and (ii) an inhibitor of the anti-coagulation effect of heparin or a pharmaceutically-acceptable salt thereof, such as any of those described herein. The method can at least partially inhibit metastasis. The composition administered may contain an amount of the heparin preparation effective to inhibit metastasis and an amount of the inhibitor of the anti-coagulation activity of heparin effective to at least partially, for example, at least substantially, inhibit the anti-coagulation activity of the heparin preparation (while both components are in the body).

A related embodiment of the invention provides a method for treating a cancer susceptible to metastasis in a mammal such as a human that includes the step of:

administering, for example co-administering, to a mammalian subject, such as a human, having/diagnosed with a cancer susceptible to metastasis (such as those described herein), for example, not yet or already metastasizing, (i) an anti-metastatic heparin preparation having anti-coagulant activity in the absence of an inhibitor thereof; and (ii) an inhibitor of the anti-coagulation effect of heparin or a pharmaceutically-acceptable salt thereof, such as any of those described herein such that the presence of the heparin preparation and the inhibitor in the mammalian subject are temporally overlapping. The method can at least partially inhibit metastasis. The heparin preparation may be administered in an amount effective to inhibit metastasis and the inhibitor of the anti-coagulation activity of heparin may be administered in an amount effective to at least partially, for example, at least substantially, inhibit the anti-coagulation activity of the heparin preparation (while both components are in the body.)

The mammalian subject in the aforementioned methods for treating cancer may not be in need of treatment for pathological coagulation or not be in need of anti-coagulation generally. Administration may, for example, include intravenous administration or injection, such as subcutaneous or intramuscular bolus injection. Administration may, for example, begin before a patient undergoes surgery and/or radiation to resect or treat the cancer or immediately after the patient undergoes such surgery or radiation. Administration may begin before such surgery or radiation and continue after such surgery or radiation. Administration may, for example, begin before, during or after (such as immediately or proximally after) a patient undergoes cytotoxic chemotherapy for the cancer. Administration may begin before such cytotoxic chemotherapy begins and continue after the chemotherapy. Administration may be concurrent with cytotoxic chemotherapy. Each of the methods for treating cancer may further include administering at least one anticancer pharmaceutical compound, such as but not limited to a cytotoxic agent or therapeutic antibody or soluble receptor, that is not a heparin or an inhibitor of the anticoagulation effect of heparin. Said anticancer pharmaceutical compound may, for example, be one used in the art to treat the cancer that the subject has or has been diagnosed with.

The inhibitor of the anti-coagulation of heparin in embodiments of the present invention may be any of the anti-heparin compounds of U.S. Pub. No. 2011/0178104 A1, such as those of Formulas I, Ia, Ia-1, Ia-2, Ia-3, II, IIa, III, IV, or V, or pharmaceutically acceptable salts thereof.

The inhibitor of the anticoagulation effect of heparin may, for example, be a compound of any one of Formulas I, II, IIa, III, IV or V, or a pharmaceutically acceptable salt thereof, as set forth below.

The inhibitor of the anticoagulation effect of heparin may, for example, be a compound of Formula I or a pharmaceutically acceptable salt thereof:

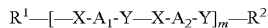    I or pharmaceutically acceptable salt thereof, wherein:
each X is, independently, $NR^8$;
each Y is C=O;
each $R^8$ is, independently, hydrogen or alkyl;
each $A_2$ is optionally substituted arylene or optionally substituted heteroarylene, and
each $A_1$ is —$(CH_2)_q$-, wherein q is 1 to 7, wherein $A_1$ and $A_2$ are each, independently, optionally substituted with one or more PL group(s), one or more NPL group(s), or a combination of one or more PL group(s) and one or more NPL group(s);
$R^1$ is hydrogen, a PL group, or an NPL group, and $R^2$ is —X-$A_1$-Y—$R^{11}$, wherein $R^{11}$ is hydrogen, a PL group, or an NPL group; or
$R^1$ and $R^2$ are each, independently, hydrogen, a PL group, or an NPL group; or
$R^1$ and $R^2$ together are a single bond; or
$R^1$ is —Y-$A_2$-X—$R^{12}$, wherein $R^{12}$ is hydrogen, a PL group, or an NPL group, and $R^2$ is hydrogen, a PL group, or an NPL group;
each NPL group is, independently, —$B(OR^4)_2$ or —$(NR3')_{q1NPL}$-$U^{NPL}$-$LK^{NPL}$-$(NR3'')_{q2NPL}$—R4', wherein:
$R^3$, $R^{3'}$, and $R^{3''}$ are each, independently, hydrogen, alkyl, or alkoxy;
$R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substituents, wherein each substituent is, independently, alkyl, halo, or haloalkyl;
each $U^{NPL}$ is, independently, absent or O, S, S(=O), S(=O)2, $NR^3$, —C(=O)—, —C(=O)—$NR^3$—, —C(=O)—N=N—$NR^3$—, —C(=O)—$NR^3$—N=N—, —N=N—$NR^3$—, —C(=N—N($R^3$)2-), C(=$NR^3$)—, —C(=O)O—, —C(=O)S—, —C(=S)—, —O—P(=O)2O-, —S—C=N—, or —C(=O)—$NR^3$—O—, wherein groups with two chemically nonequivalent termini can adopt both possible orientations;
each $LK^{NPL}$ is, independently, —$(CH_2)_{pNPL}$— and $C_{2-8}$ alkenylenyl, wherein each of the $(CH_2)_{pNPL}$ and $C_{2-8}$ alkenylenyl is optionally substituted with one or more substituents, wherein each substituent is, independently, amino, hydroxyl, aminoalkyl, hydroxylalkyl, or alkyl;
each pNPL is, independently, an integer from zero to 8;
q1NPL and q2NPL are each, independently, zero, 1, or 2;
each PL group is, independently, halo, hydroxyethoxymethyl, methoxyethoxymethyl, polyoxyethylene, or —$(NR^{5'})_{q1PL}$—$U^{PL}$-$LK^{PL}$-$(NR^{5''})_{q2PL}$—V, wherein:
$R^5$, $R^{5'}$, and $R^{5''}$ are each, independently, hydrogen, alkyl, or alkoxy; each $U^{PL}$ is, independently, absent or O, S, S(=O), S(=O)$_2$, $NR^5$, —C(=O)—, —C(=O)—$NR^5$—, —C(=O)—N=N—$NR^5$—, —C(=O)—$NR^5$—N=N—, —N=N—$NR^5$—, —C(=N—N($R^5$)2)-, —C(=$NR^5$)—, —C(=O)O—, —C(=O)S—, —C(=S)—, —O—P(=O)$_2$O—, —S—C=N—, or —C(=O)—$NR^5$—O—, wherein groups with two chemically nonequivalent termini can adopt either of the two possible orientations;
each V is, independently, nitro, cyano, amino, halo, hydroxy, alkoxy, alkylthio, alkylamino, dialkylamino, —$NH(CH2)_pNH_2$ wherein p is 1 to 5, —C(=O)NH$(CH_2)_pNH_2$ wherein p is 1 to 5, —C(=O)NH$(CH_2)_p$NHC(=NH)NH$_2$ wherein p is 1 to 5, C(=O)NH$(CH_2)_p$ NHC(=O)NH$_2$ wherein p is 1 to 5, —NHC(=O)-alkyl, —$N(CH_2CH_2NH_2)_2$, diazamino, amidino, guanidino, ureido, carbamoyl, —C(=O)OH, —C(=O)$OR^c$, —C(=O)NH—OH, —O—NH—C(=NH)NH$_2$, —NH—S(=O)$_2$OH, S(=O)$_2$OH, $NR^dR^e$, semicarbazone, aryl, cycloalkyl, heterocycloalkyl, or heteroaryl, wherein each of the aryl and cycloalkyl is substituted with one or more substituents, wherein each of the heterocycloalkyl and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, —$NH(CH_2)_pNH_2$ wherein p is 1 to 5, —$N(CH_2CH_2NH_2)_2$, diazamino, amidino, guanidino, ureido, carbamoyl, —C(=O)OH, C(=O)$OR^c$, —C(=O)NH—OH, —O—NH—C(=NH)NH$_2$, —NH—S(=O)$_2$OH, S(=O)$_2$OH, $NR^dR^e$, semicarbazone, aminosulfonyl, aminoalkoxy, aminoalkythio, lower acylamino, or benzyloxycarbonyl;
each $R^e$ is, independently, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more substituents, wherein each substituent is, independently, OH, amino, halo, $C_{1-6}$ alkyl, $C_{1-6}$ haloalkyl, aryl, arylalkyl, heteroaryl, heteroarylalkyl, cycloalkyl, or heterocycloalkyl;
$R^d$ and $R^e$ are, independently, H, $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the $C_{1-6}$ alkyl, $C_{1-6}$ haloalkyl, $C_{2-6}$ alkenyl, $C_{2-6}$ alkynyl, aryl, heteroaryl, cycloalkyl, heterocycloalkyl, aryl alkyl, heteroaryl alkyl, cycloalkylalkyl and heterocycloalkylalkyl is optionally substituted by OH, amino, halo, $C_{1-6}$ alkyl, $C_{1-6}$ haloalkyl, aryl, arylalkyl, heteroaryl, heteroarylalkyl, cycloalkyl, or heterocycloalkyl;

or $R^d$ and $R^e$ together with the N atom to which they are attached form a 4-, 5-, 6-, 7-, or 8-membered heterocycloalkyl;

each $LK^{PL}$ is, independently, —$(CH_2)_{pPL}$— or $C_{2-8}$ alkenylenyl, wherein each of the —$(CH_2)_{pPL}$— and $C_{2-8}$ alkenylenyl is optionally substituted with one or more substituents, wherein each substituent is, independently, amino, hydroxyl, aminoalkyl, hydroxylalkyl, or alkyl;

each pPL is, independently, an integer from zero to 8;

q1PL and q2PL are each, independently, zero, 1, or 2;

m is an integer from 1 to about 20; and at least one of $A_1$ is a —$(CH_2)_q$— group substituted with one substituent, wherein the substituent is $(CH_2)$—$V^1$, $(CH_2)_2$—$V^1$, —$(CH_2)_3$—$V^1$, —$(CH_2)_4$—$V^1$, or —$(CH_2)_5$—$V^1$, wherein $V^1$ is indolyl.

The inhibitor of the anti-coagulation activity of heparin may, for example, be a compound of Formula I or a pharmaceutically acceptable salt thereof, further in which:

each X is NH;

each $A_2$ is, independently, phenyl optionally substituted with one or more substituents, wherein each substituent is, independently, O—$(CH_3)$, halo, or O—$(CH_2)_2$—V;

each $A_1$ is, independently, a —$(CH_2)$— group optionally substituted with one substituent, wherein the substituent is $CH_3$, —$(CH_2)$—V, —$(CH_2)_2$—V, —$(CH_2)_3$—V, —$(CH_2)_4$—V, or —$(CH_2)_5$—V;

each V is, independently, hydroxyl, amino, heteroarylamino, ureido, guanidino, carbamoyl, C(=O)OH, —C(=O)$OR^e$, —C(=O)NH—OH, —O—NH—C(=NH)$NH_2$, —NH—S(=O)$_2$OH, S(=O)$_2$OH, aziridinyl, azetidinyl, pyrrolidinyl, piperidinyl, piperazinyl, morpholino, azepanyl, azocanyl, tetrazolyl, 1,2,4-oxadiazolyl, 1,3,4-oxadiazolyl, imidazolyl, pyridinyl, indolyl, or a substituted phenyl, wherein the substituted phenyl is substituted with one or more substituents, wherein each substituent is, independently, OH or amino; and at least one of $A_1$ is a —$(CH_2)$— group substituted with one substituent, wherein the substituent is $(CH_2)$—$V^1$, $(CH_2)_2$—$V^1$, —$(CH_2)_3$—$V^1$, —$(CH_2)_4$—$V^1$, or —$(CH_2)_5$—$V^1$, wherein $V^1$ is indolyl.

The heparin binding compound of Formula I may be a heparin binding compound of Formula Ia as follows:

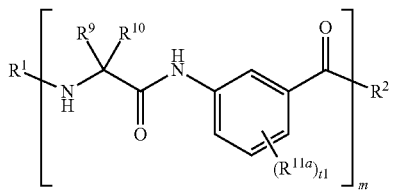

Ia or a pharmaceutically-acceptable salt thereof, wherein $R^1$ is hydrogen, an amino acid connected by its carbonyl group, —C(=$NR^3$)—$NR^{3''}R^{4'}$, —C(=O)—$(CH_2)_{pNPL}$—$R^{4'}$, —C(=O)—$(CH_2)_{pPL1}$—V, —C(=O)-$A_2$-NH—C(=O)—$(CH_2)_{pPL1}$V, or —C(=O)-$A_2$-NH—C(=O)—$(CH_2)_{pNPL}$—$R^{4'}$;

$R^3$ and $R^{3''}$ are each, independently, hydrogen, alkyl, or alkoxy;

$R^{4'}$ is hydrogen, alkyl, alkenyl, alkynyl, cycloalkyl, aryl, or heteroaryl, each of which is optionally substituted with one or more substituents, wherein each substituent is, independently, alkyl, halo, or haloalkyl;

each pNPL is, independently, an integer from 0 to 8;

pPL1 is an integer from 1 to 5; and $A_2$ is optionally substituted arylene or optionally substituted heteroarylene, wherein $A_2$ is optionally substituted with one or more PL groups, one or more NPL groups, or a combination of one or more PL groups and one or more NPL groups;

$R^2$ is OH, $OR^{600}$, $NH_2$, $NHR^{600}$, $N(R^{600})_2$, an amino acid connected by its amino group, an α amino acid amide connected by its α amino group, —NH—$(CH_2)_{pPL2}$—V, or —NH-$A_1$-C(=O)—$NH_2$;

each $R^{600}$ is, independently, unsubstituted alkyl or aryl, or either alkyl or aryl substituted with OH, halo, cyan, nitro, amino, alkoxy, alkylthio, alkylamino, or dialkylamino;

pPL2 is an integer from 1 to 5; and $A_1$ is optionally substituted arylene or optionally substituted heteroarylene, wherein $A_1$ is optionally substituted with one or more PL groups, one or more NPL groups, or a combination of one or more PL groups and one or more NPL groups;

each $R^9$ is, independently, H, a PL group, or an NPL group;

each $R^{10}$ is, independently, H, a PL group, or an NPL group;

or $R^9$ and $R^{10}$, taken together, constitute the side chain of a D or L α amino acid;

each $R^{11a}$ is, independently, a PL group or an NPL group;

each NPL group is, independently, —$B(OR^{40})_2$ or —$(NR^3)_{q1NPL}$—$U^{NPL}$-$LK^{NPL}$-$(NR^{3''})_{q2NPL}$—$R^{40'}$;

$R^{3'}$ is hydrogen, alkyl, or alkoxy;

$R^{40}$ and $R^{40'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substituents, wherein each substituent is, independently, alkyl, halo, or haloalkyl;

each $U^{NPL}$ is, independently, absent or O, S, S(=O), S(=O)$_2$, $NR^3$, —(C=O)—, —C(=O)—$NR^3$—, —C(=O)—N=N—$NR^3$—, —C(=O)—$NR^3$—N=N—, —N=N—$NR^3$—, —C(=N—$N(R^3)_2$)—, —C(=$NR^3$)—, —C(=O)O—, —C(=O)S—, —C(=S)—, —O—P(=O)$_2$O—, —S—C=N—, or —C(=O)—$NR^3$—O—, wherein groups with two chemically nonequivalent termini can adopt both possible orientations;

each $LK^{NPL}$ is, independently, —$(CH_2)_{pNPL}$— or $C_{2-8}$alkenylenyl, wherein each of the $(CH_2)_{pNPL}$ and $C_{2-8}$alkenylenyl is optionally substituted with one or more substituents, wherein each substituent is, independently, amino, hydroxyl, aminoalkyl, hydroxylalkyl, or alkyl;

q1NPL and q2NPL are each, independently, 0, 1, or 2;

each PL group is, independently, halo, hydroxyethoxymethyl, methoxyethoxymethyl, polyoxyethylene, or —$(NR^{5'})_{q1PL}$—$U^{PL}$-$LK^{PL}$-$(NR^{5''})_{q2PL}$—V, wherein:

$R^{5'}$ and $R^{5''}$ are each, independently, hydrogen, alkyl, or alkoxy;

each $U^{PL}$ is, independently, absent or O, S, S(=O), S(=O)$_2$, $NR^5$, —C(=O)—, —C(=O)—$NR^5$—, —C(=O)—N=N—$NR^5$—, —C(=O)—$NR^5$—N=N—, —N=N—$NR^5$—, —C(=N—$N(R^5)_2$)—, —C(=$NR^5$)—, —C(=O)O—, —C(=O)S—, —C(=S)—, —O—P(=O)$_2$O—, —S—C=N—, or —C(=O)—$NR^5$—O—, wherein groups with two chemically nonequivalent termini can adopt either of the two possible orientations;

each V is, independently, nitro, cyano, amino, halo, hydroxy, alkoxy, alkylthio, alkylamino, dialkylamino, amido, alkylamido, dialkylamido, —NH(CH$_2$)$_p$NH$_2$ wherein p is 1 to 5, —C(=O)NH(CH$_2$)$_p$NH$_2$ wherein p is 1 to 5, —C(=O)NH(CH$_2$)$_p$NHC(=NH)NH$_2$ wherein p is 1 to 5, —C(=O)NH(CH$_2$)$_p$NHC(=O)NH$_2$ wherein p is 1 to 5, —NHC(=O)-alkyl, —N(CH$_2$CH$_2$NH$_2$)$_2$, diazamino, amidino, guanidino, ureido, carbamoyl, —C(=O)OH, —C(=O)OR$^c$, —C(=O)NH—OH, —O—NH—C(=NH)NH$_2$, —NH—S(=O)$_2$OH, —S(=O)$_2$OH, NR$^d$R$^e$, semicarbazone, aryl, cycloalkyl, heterocycloalkyl, or heteroaryl, wherein each of the aryl and cycloalkyl is substituted with one or more substituents, wherein each of the heterocycloalkyl and heteroaryl is optionally substituted with one or more substituents, and wherein each of the substituents for the aryl, cycloalkyl, heterocycloalkyl, and heteroaryl is, independently, nitro, cyano, amino, halo, hydroxy, alkoxy, alkylthio, alkylamino, dialkylamino, —NH(CH$_2$)$_p$NH$_2$ wherein p is 1 to 5, —N(CH$_2$CH$_2$NH$_2$)$_2$, diazamino, amidino, guanidino, ureido, carbamoyl, —C(=O)OH, —C(=O)OR$^c$, —C(=O)NH—OH, —O—NH—C(=NH)NH$_2$, —NH—S(=O)$_2$OH, S(=O)$_2$OH, NR$^d$R$^e$, semicarbazone, aminosulfonyl, aminoalkoxy, aminoalkythio, lower acylamino, or benzyloxycarbonyl;

each R$^c$ is, independently, C$_{1-6}$alkyl, C$_{1-6}$haloalkyl, C$_{2-6}$alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, C$_{1-6}$ alkyl, C$_{1-6}$haloalkyl, aryl, arylalkyl, heteroaryl, heteroarylalkyl, cycloalkyl, or heterocycloalkyl;

R$^d$ and R$^e$ are, independently, H, C$_{1-6}$alkyl, C$_{1-6}$haloalkyl, C$_{2-6}$alkenyl, C$_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the C$_{1-6}$alkyl, C$_{1-6}$haloalkyl, C$_{2-6}$alkenyl, C$_{2-6}$alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, C$_{1-6}$alkyl, C$_{1-6}$haloalkyl, C$_{1-6}$haloalkyl, aryl, arylalkyl, heteroaryl, heteroarylalkyl, cycloalkyl, or heterocycloalkyl;

or R$^d$ and R$^e$ together with the N atom to which they are attached form a 4-, 5-, 6-, 7-, or 8-membered heterocycloalkyl;

each LK$^{PL}$ is, independently —(CH$_2$)$_{pPL3}$— or C$_{2-8}$alkenylenyl, wherein each of the —(CH$_2$)$_{pPL3}$— or C$_{2-8}$alkenylenyl is optionally substituted with one or more substituents, wherein each substituent is, independently, amino, hydroxyl, aminoalkyl, hydroxylalkyl, or alkyl;

each pPL3 is, independently, an integer from 0 to 8;
q1PL and q2PL are each, independently, 0, 1, or 2;
each t1 is, independently, 0, 1, or 2; and
m is an integer from 1 to 20.

In some embodiments of the compound of Formula Ia or pharmaceutically acceptable salt thereof, the compound is a compound of Formula Ia-1, Ia-2, or Ia-3:

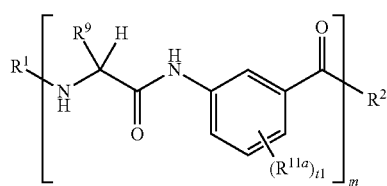

Ia-1

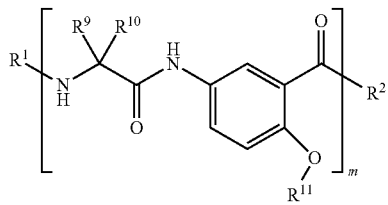

Ia-2

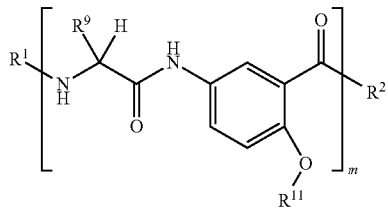

Ia-3 or a pharmaceutically acceptable salt thereof, wherein each R" is, independently, H, alkyl, haloalkyl, or —(CH2)ppL-V, wherein pPL is an integer from 1 to 5.

In some embodiments of the compound of Formula Ia-2 or Ia-3, or pharmaceutically acceptable salt thereof, each R" is, independently, alkyl. In some embodiments, each R$^{11}$ is methyl.

In another embodiment, the inhibitor of the anti-coagulation activity of heparin of Formula Ia is a compound having Formula Ia-4, as follows:

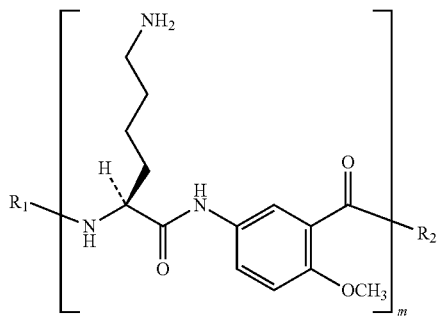

Ia-4 or a pharmaceutically acceptable salt thereof.

The inhibitor of the anti-coagulation activity of heparin may, for example, be a compound of Formula II or a pharmaceutically acceptable salt thereof, as follows:

$$R^1—[—X-A_1-X—Y-A_2-Y—]_m—R^2 \qquad \text{II}$$

or pharmaceutically acceptable salt thereof, wherein:
each X is, independently, NR$^8$, O, S, —N(R$^8$)N(R$^8$)—, —N(R$^8$)—(N=N)—, —(N=N)—N(R$^8$)—, —C(R$^7$R$^{7\prime}$)NR$^8$—, —C(R$^7$R$^{7\prime}$)O—, or —C(R$^7$R$^{7\prime}$)S—;
each Y is, independently, C=O, C=S, O=S=O, —C(=O)C(=O)—, C(R$^6$R$^{6\prime}$)C=O, or C(R$^6$R$^{6\prime}$)C=S;
each R$^8$ is, independently, hydrogen or alkyl;
each R$^7$ and each R$^{7\prime}$ are, independently, hydrogen or alkyl; or R$^7$ and R$^{7\prime}$ together form —(CH$_2$)$_p$—, wherein p is 4 to 8;
each R$^6$ and each R$^{6\prime}$ are, independently, hydrogen or alkyl; or R$^6$ and R$^{6\prime}$ together form —(CH$_2$)$_2$NR$^{12}$(CH$_2$)$_2$—, wherein R$^{12}$ is hydrogen, —C(=N)CH$_3$, or —C(=NH)—NH$_2$;

A₁ and A₂ are each, independently, optionally substituted arylene or optionally substituted heteroarylene, wherein A₁ and A₂ are each, independently, optionally substituted with one or more PL group(s), one or more NPL group(s), or a combination of one or more PL group(s) and one or more NPL group(s);

or each A₂ is, independently, optionally substituted arylene or optionally substituted heteroarylene, and each A₁ is, independently, optionally substituted C3 to C8 cycloalkyl, wherein A₁ and A₂ are each, independently, optionally substituted with one or more PL group(s), one or more NPL group(s), or a combination of one or more PL group(s) and one or more NPL group(s);

$R^1$ is hydrogen, a PL group, or an NPL group, and $R^2$ is —X-A₁-X—$R^1$, wherein A₁ is as defined above and is optionally substituted with one or more PL group(s), one or more NPL group(s), or a combination of one or more PL group(s) and one or more NPL group(s); or $R^1$ is hydrogen, a PL group, or an NPL group, and $R^2$ is —X-A'-X—$R^1$, wherein A' is $C_3$ to $C_8$ cycloalkyl, aryl, or heteroaryl and is optionally substituted with one or more PL group(s), one or more NPL group(s), or a combination of one or more PL group(s) and one or more NPL group(s); or $R^1$ is —Y-A₂-Y—$R^2$, and $R^2$ is each, independently, hydrogen, a PL group, or an NPL group; or $R^1$ is —Y-A' and $R^2$ is —X-A', wherein each A' is independently $C_3$ to $C_8$ cycloalkyl, aryl, or heteroaryl, and is optionally substituted with one or more PL group(s), one or more NPL group(s), or a combination of one or more PL group(s) and one or more NPL group(s); or $R^1$ and $R^2$ are, independently, a PL group, or an NPL group; or $R^1$ and $R^2$ together form a single bond;

each NPL is, independently, —B(OR⁴)₂ or —(NR³')$q1_{NPL}$-U$^{NPL}$-LK$^{NPL}$-(NR³")$_{q2NPL}$—R4', wherein:

$R^3$, $R^{3'}$, and $R^{3''}$ are each, independently, hydrogen, alkyl, or alkoxy;

$R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more alkyl or halo groups;

each $U^{NPL}$ is, independently, absent or O, S, S(=O), S(=O)₂, NR³, —C(=O)—, C(=O)—NR³—, —C(=O)—N=N—NR³—, —C(=O)—NR³—N=N—, —N=N—NR³—, —C(=N—N(R³)₂)—, C(=NR³)—, —C(=O)O—, —C(=O)S—, —C(=S)—, —O—P(=O)₂O—, —S—C=N—, or —C(=O)—NR³—O—, wherein groups with two chemically nonequivalent termini can adopt both possible orientations;

each LK$^{NPL}$ is, independently, —(CH₂)$_{pNPL}$— or $C_{2-8}$alkenylenyl, wherein each of the —(CH₂)$_{pNPL}$— and $C_{2-8}$alkenylenyl is optionally substituted with one or more substituents, wherein each substituent is, independently, amino, hydroxyl, aminoalkyl, hydroxylalkyl, or alkyl;

each pNPL is, independently, an integer from zero to 8;

q1NPL and q2NPL are each, independently, zero, 1, or 2;

each PL is, independently, halo, hydroxyethoxymethyl, methoxyethoxymethyl, polyoxyethylene, or —(NR⁵')$_{q1PL}$—U$^{PL}$-LK$^{PL}$-(NR⁵")$_{q2pL}$—V, wherein:

$R^5$, $R^{5'}$, and $R^{5''}$ are each, independently, hydrogen, alkyl, or alkoxy;

each $U^{PL}$ is, independently, absent or O, S, S(=O), S(=O)₂, NR⁵, —C(=O)—, —C(=O)—NR⁵—, —C(=O)—N=N—NR⁵—, —C(=O)—NR⁵—N=N—, —N=N—NR⁵—, —C(=N—N(R⁵)₂)—, C(=NR⁵)—, —C(=O)O—, —C(=O)S—, —C(=S)—, —O—P(=O)₂O—, —S—C=N—, or —C(=O)—NR⁵—O—, wherein groups with two chemically nonequivalent termini can adopt both possible orientations;

each V is, independently, nitro, cyano, amino, hydroxy, alkoxy, alkylthio, alkylamino, dialkylamino, —NH(CH₂)$_p$NH₂ wherein p is 1 to 5, C(=O)NH(CH₂)$_p$NH₂ wherein p is 1 to 5, —C(=O)NH(CH₂)$_p$NHC(=NH)NH₂ wherein p is 1 to 5, —C(=O)NH(CH₂)$_p$NHC(=O)NH₂ wherein p is 1 to 5, —NHC(=O)-alkyl, —N(CH₂CH₂NH2)₂, diazamino, amidino, guanidino, ureido, carbamoyl, —C(=O)OH, —C(=O)OR$^c$, —C(=O)NH—OH, —O—NH—C(=NH)NH₂, —NH—S(=O)₂OH, S(=O)₂OH, NR$^d$R$^e$, semicarbazone, aryl, cycloalkyl, heterocycloalkyl, or heteroaryl, wherein each of the aryl and cycloalkyl is substituted with one or more substituents, wherein each of the heterocycloalkyl, and heteroaryl is optionally substituted with one or more substituents, and wherein each of the subsituents for the aryl, cycloalkyl, heterocycloalkyl, and heteroaryl is, independently, nitro, cyano, amino, hydroxy, alkoxy, alkylthio, alkylamino, dialkylamino, —NH(CH₂)$_p$NH₂ wherein p is 1 to 5, —N(CH₂CH₂NH₂)₂, diazamino, amidino, guanidino, ureido, carbamoyl, —C(=O)OH, C(=O)OR$^c$, —C(=O)NH—OH, —O—NH—C(=NH)NH₂, —NH—S(=O)₂OH, S(=O)₂OH, NR$^d$R$^e$, semicarbazone, aminosulfonyl, aminoalkoxy, aminoalkythio, lower acylamino, or benzyloxycarbonyl;

each LK$^{PL}$ is, independently, —(CH2)$_{pPL}$ or $C_{2-8}$alkenylenyl, wherein each of the —(CH₂)$_{pPL}$ and $C_{2-8}$alkenylenyl is optionally substituted with one or more substituents, wherein each substituent is, independently, amino, hydroxyl, aminoalkyl, hydroxylalkyl, or alkyl;

each pPL is, independently, an integer from zero to 8;

q1PL and q2PL are each, independently, zero, 1, or 2; and m is an integer from 1 to about 20.

The compound of Formula II, or pharmaceutically salt thereof, may be a compound of Formula IIa, or a pharmaceutically acceptable salt thereof, as follows:

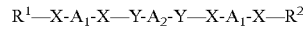    IIa or a pharmaceutically acceptable salt thereof, wherein:

each X is, independently, NR⁸, O, S, or —N(R⁸)N(R⁸)—;

each Y is, independently, C=O, C=S, or O=S=O;

each $R^8$ is, independently, hydrogen or alkyl;

A₁ and A₂ are each, independently, optionally substituted arylene or optionally substituted heteroarylene, wherein A₁ and A₂ are each, independently, optionally substituted with one or more PL group(s), one or more NPL group(s), or a combination of one or more PL group(s) and one or more NPL group(s);

$R^1$ is a PL group or an NPL group;

$R^2$ is $R^1$ or the same as $R^1$;

each NPL is —(NR³')$_{q1NP}$—U$^{NPL}$-LK$^{NPL}$-(NR³")$_{q2NPL}$—R⁴', wherein:

$R^3$, $R^{3'}$, and $R^{3''}$ are each, independently, hydrogen, alkyl, or alkoxy;

$R^4$ and $R^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more alkyl or halo groups;

$U^{NPL}$ is independently, absent or O, S, S(=O), S(=O)$_2$, NR$^3$, —C(=O)—, —C(=O)—NR$^3$—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —S—C=N—, or —C(=O)—NR$^3$—O—, wherein groups with two chemically nonequivalent termini can adopt either of the two possible orientations;

each $LK^{NPL}$ is, independently, —(CH$_2$)$_{pNPL}$— or C$_{2-8}$alkenylenyl, wherein the —(CH$_2$)$_{pNPL}$— is optionally substituted with one or more substituents, wherein each substituent is, independently, amino, hydroxyl, or alkyl;

each pNPL is, independently, an integer from zero to 8;

q1NPL and q2NPL are each, independently, zero, 1, or 2;

each PL is, independently, halo, hydroxyethoxymethyl, methoxyethoxymethyl, polyoxyethylene, or —(NR$^{5'}$)$_{q1PL}$—U$^{PL}$-LK$^{PL}$-(NR$^{5''}$)$_{q2PL}$—V, wherein:

R$^5$, R$^{5'}$, and R$^{5''}$ are each, independently, hydrogen, alkyl, or alkoxy;

each $U^{PL}$ is, independently, absent or O, S, S(=O), S(=O)$_2$, NR$^5$, —C(=O)—, —C(O)—NR$^5$—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N—, or —C(=O)—NR$^5$—O—, wherein groups with two chemically nonequivalent termini can adopt both possible orientations;

each V is, independently, nitro, cyano, amino, hydroxy, alkoxy, alkylthio, alkylamino, dialkylamino, —NH(CH$_2$)$_p$NH$_2$ wherein p is 1 to 5, —C(=O)NH(CH$_2$)$_p$NH$_2$ wherein p is 1 to 5, —C(=O)NH(CH$_2$)$_p$NHC(=NH)NH$_2$ wherein p is 1 to 5, —C(=O)NH(CH$_2$)$_p$NHC(=O)NH$_2$ wherein p is 1 to 5, —NHC(=O)-alkyl, —N(CH$_2$CH$_2$NF12)2, diazamino, amidino, guanidino, ureido, carbamoyl, —C(=O)OH, —C(=O)OR$^e$, —C(=O)NH—OH, —O—NH—C(=NH)NH$_2$, —NH—S(=O)$_2$OH, S(=O)2OH, NR$^d$R$^e$, semicarbazone, aryl, heterocycloalkyl, or heteroaryl, wherein the aryl is substituted with one or more substituents, wherein each of the heterocycloalkyl and heteroaryl is optionally substituted with one or more substituents, and wherein each of each of the substituents for the aryl, heterocycloalkyl, and heteroaryl is, independently, nitro, cyano, amino, hydroxy, alkoxy, alkylthio, alkylamino, dialkylamino, —NH(CH$_2$)$_p$NH$_2$ wherein p is 1 to 5, —N(CH$_2$CH$_2$NH$_2$)$_2$, diazamino, amidino, guanidino, ureido, carbamoyl, —C(=O)OH, —C(=O)OR$^e$, —C(O)NH—OH, —O—NH—C(=NH)NH$_2$, NH—S(=O)$_2$OH, S(=O)$_2$OH, NR$^d$R$^e$, semicarbazone, aminosulfonyl, aminoalkoxy, aminoalkythio, lower acylamino, or benzyloxycarbonyl;

each $LK^{PL}$ is, independently, —(CH$_2$)$_{pPL}$— or C$_{2-8}$alkenylenyl, wherein the —(CH$_2$)$_{pNPL}$— is optionally substituted with one or more substituents, wherein each substituent is, independently, amino, hydroxyl, or alkyl;

each pPL is, independently, an integer from zero to 8; and q1PL and q2PL are each, independently, zero, 1, or 2.

The inhibitor of the anticoagulation activity of heparin may, for example, be a compound of Formula III or a pharmaceutically acceptable salt thereof, as follows:

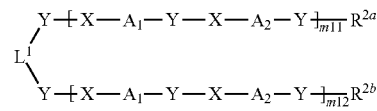

III or a pharmaceutically acceptable salt thereof, wherein:

each X is, independently, NR$^8$;

each Y is C=O;

each R$^8$ is, independently, hydrogen or alkyl;

each A$_2$ is optionally substituted arylene or optionally substituted heteroarylene, and each A$_1$ is —(CH$_2$)$_q$—, wherein q is 1 to 7, wherein A$_1$ and A$_2$ are each, independently, optionally substituted with one or more PL group(s), one or more NPL group(s), or a combination of one or more PL group(s) and one or more NPL group(s);

R$^2$ and R$^{2a}$ are each, independently, hydrogen, a PL group, an NPL group, or X-A$_1$-Y—R$^{11}$, wherein R$^{11}$ is hydrogen, a PL group, or an NPL group;

L$^1$ is C$_{1-10}$ alkylene optionally substituted with one or more substituents, wherein each substituent is, independently, alkyl, halo, haloalkyl, aminoalkyl, hydroxylalkyl, V, or —(CH2)$_{pPL}$-V wherein pPL is an integer from 1 to 5;

each NPL group is, independently, —B(OR$^4$)$_2$ or —(NR3')$_{q1NPL}$-U$^{NPL}$-LK$^{NPL}$-(NR$^{3''}$)$_{q2NPL}$—R$^{4'}$, wherein:

R$^3$, R$^{3'}$, and R$^{3''}$ are each, independently, hydrogen, alkyl, or alkoxy;

R$^4$ and R$^{4'}$ are each, independently, hydrogen, alkyl, alkenyl, alkynyl, cycloalkyl, aryl, and heteroaryl, wherein each of the alkyl, alkenyl, alkynyl, cycloalkyl, aryl, or heteroaryl is optionally substituted with one or more substituents, wherein each substituent is, independently, alkyl, halo, or haloalkyl;

each $U^{NPL}$ is, independently, absent or O, S, S(=O), S(=O)$_2$, NR$^3$, —C(=O)—, —C(=O)—NR$^3$—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —S—CN—, or —C(=O)—NR$^3$—O—, wherein groups with two chemically nonequivalent termini can adopt both possible orientations;

each $LK^{NPL}$ is, independently, —(CH$_2$)$_{pNPL}$— or C$_{2-8}$alkenylenyl, wherein each of the —(CH$_2$)$_{pNPL}$— and C$_{2-8}$alkenylenyl is optionally substituted with one or more substituents, wherein each substituent is, independently, amino, hydroxyl, aminoalkyl, hydroxylalkyl, or alkyl;

each pNPL is, independently, an integer from zero to 8;

q1NPL and q2NPL are each, independently, zero, 1, or 2;

each PL group is, independently, halo, hydroxyethoxymethyl, methoxyethoxymethyl, polyoxyethylene, or —(NR$^{5'}$)$_{q1NPL}$—U$^{PL}$-LK$^{PL}$-(NR$^{5''}$)$_{q2PL}$—V, wherein:

R$^5$, R$^{5'}$, and R$^{5''}$ are each, independently, hydrogen, alkyl, or alkoxy;

each $U^{PL}$ is, independently, absent or O, S, S(=O), S(=O)$_2$, NR$^5$, —C(=O)—, —C(=O)—NR$^5$—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —S—C=N—, or —C(=O)—NR⁵—O—, wherein groups with two chemically nonequivalent termini can adopt either of the two possible orientations;

each V is, independently, nitro, cyano, amino, halo, hydroxy, alkoxy, alkylthio, alkylamino, dialkylamino, —NH(CH₂)$_p$NH₂ wherein p is 1 to 5, —C(=O)NH(CH₂)$_p$NH₂ wherein p is 1 to 5, —C(=O)NH(CH₂)$_p$NHC(=NH)NH₂ wherein p is 1 to 5, —C(=O)NH(CH₂)$_p$NHC(=O)NH2 wherein p is 1 to 5, —NHC(=O)-alkyl, —N(CH₂CH₂NH₂)₂, diazamino, amidino, guanidino, ureido, carbamoyl, —C(=O)OH, —C(=O)OR$^c$, —C(=O)NH—OH, —O—NH—C(=NH)NH₂, —NH—S(=O)₂OH, S(=O)₂OH, NR$^d$R$^e$, semicarbazone, aryl, cycloalkyl, heterocycloalkyl, or heteroaryl, wherein each of the aryl and cycloalkyl is substituted with one or more substituents, wherein each of the heterocycloalkyl and heteroaryl is optionally substituted with one or more substituents, and wherein each of the subsituents for the aryl, cycloalkyl, heterocycloalkyl, and heteroaryl is, independently, nitro, cyano, amino, halo, hydroxy, alkoxy, alkylthio, alkylamino, dialkylamino, —NH(CH₂)$_p$NH₂ wherein p is 1 to 5, —N(CH₂CH₂NH₂)₂, diazamino, amidino, guanidino, ureido, carbamoyl, —C(=O)OH, —C(=O)OR$^c$, —C(=O)NH—OH, —O—NH—C(=NH)NH₂, —NH—S(=O)₂OH, S(=O)₂OH, NR$^d$R$^e$, semicarbazone, aminosulfonyl, aminoalkoxy, aminoalkythio, lower acylamino, or benzyloxycarbonyl;

each R$^e$ is, independently, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, C$_{1-6}$ alkyl, C$_{1-6}$ haloalkyl, aryl, arylalkyl, heteroaryl, heteroarylalkyl, cycloalkyl, or heterocycloalkyl;

R$^d$ and R$^e$ are, independently, H, C$_{1-6}$ alkyl, C$_{1-6}$haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the C$_{1-6}$ alkyl, C$_{1-6}$ haloalkyl, C$_{2-6}$ alkenyl, C$_{2-6}$ alkynyl, aryl, heteroaryl, cycloalkyl, heterocycloalkyl, aryl alkyl, heteroaryl alkyl, cycloalkylalkyl and heterocycloalkylalkyl is optionally substituted by OH, amino, halo, C$_{1-6}$ alkyl, C$_{1-6}$ haloalkyl, aryl, arylalkyl, heteroaryl, heteroarylalkyl, cycloalkyl, or heterocycloalkyl;

or R$^d$ and R$^e$ together with the N atom to which they are attached form a 4-, 5-, 6-, 7-, or 8-membered heterocycloalkyl;

each LK$^{PL}$ is, independently, —(CH₂)$_{pPL}$— or C$_{2-8}$alkenylenyl, wherein each of the ⁻(CH₂)pPL- and C$_{2-8}$alkenylenyl is optionally substituted with one or more substituents, wherein each substituent is, independently, amino, hydroxyl, aminoalkyl, hydroxylalkyl, or alkyl;

each pPL is, independently, an integer from zero to 8
q1PL and q2PL are each, independently, zero, 1, or 2;
m11 is an integer from 1 to about 20; and
m12 is an integer from 1 to about 20.

The inhibitor of the anti-coagulation activity of heparin may, for example, be a compound of Formula III, or a pharmaceutically acceptable thereof, further in which: each moiety of —[—X-A₁-Y—X-A₂-Y—]— is, independently, a moiety of:

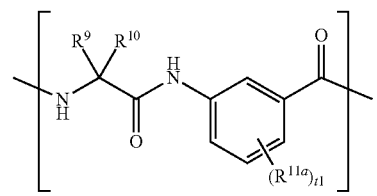

each R⁹ is, independently, H, a PL group, or an NPL group;
each R$^m$ is, independently, H, a PL group, or an NPL group;
each R$^{11a}$ is, independently, a PL group or an NPL group; and
each t1 is independently zero, 1, or 2.

The inhibitor of the anti-coagulation activity of heparin may, for example, be a compound of Formula IV, or a pharmaceutically acceptable salt thereof, as follows:

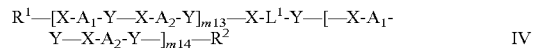
$$R^1—[X-A_1-Y—X-A_2-Y]_{m13}—X-L^1-Y—[—X-A_1-Y—X-A_2-Y—]_{m14}—R^2 \quad \text{IV}$$

or a pharmaceutically acceptable salt thereof, wherein:
each X is, independently, NR⁸;
each Y is C=O;
each R⁸ is, independently, hydrogen or alkyl;
each A₂ is optionally substituted arylene or optionally substituted heteroarylene, and each A₁ is —(CH₂)$_q$—, wherein q is 1 to 7, wherein A₁ and A₂ are each, independently, optionally substituted with one or more PL group(s), one or more NPL group(s), or a combination of one or more PL group(s) and one or more NPL group(s);
R¹ is hydrogen, a PL group, or an NPL group, and R² is —X-A₁-Y—R¹¹, wherein R¹¹ is hydrogen, a PL group, or an NPL group; or
R¹ and R² are each, independently, hydrogen, a PL group, or an NPL group; or
R¹ and R² together are a single bond; or
R¹ is —Y-A₂-X—R¹², wherein R¹² is hydrogen, a PL group, or an NPL group, and R² is hydrogen, a PL group, or an NPL group;
L¹ is C$_{1-10}$ alkylene optionally substituted with one or more substituents, wherein each substituent is, independently, alkyl, halo, haloalkyl; aminoalkyl, hydroxylalkyl, V, or (CH₂)$_{pPL}$—V wherein pPL is an integer from 1 to 5;
each V is, independently, hydroxy, amino, alkylamino, dialkylamino, —NH(CH₂)$_p$NH₂ wherein p is 1 to 5, —C(=O)NH(CH₂)$_p$NH₂ wherein p is 1 to 5, —C(=O)NH(CH₂)$_p$NHC(=NH)NH₂ wherein p is 1 to 5, —C(=O)NH(CH₂)$_p$NHC(=O)NH₂ wherein p is 1 to 5, —NHC(=O)-alkyl, —N(CH₂CH₂NH₂)₂, guanidino, amidino, ureido, carbamoyl, —C(=O)OH, —C(=O)OR$^c$, —C(=O)NH—OH, —O—NH—C(=NH)NH₂, —NH—S(O)₂OH, S(=O)₂OH, NR$^d$R$^e$, a substituted aryl group, heterocycloalkyl, or heteroaryl, wherein each of the heterocycloalkyl and heteroaryl is optionally substituted with one more substituents, wherein each substituent is, independently, amino, halo, cyano, nitro, hydroxy, —NH(CH₂)$_p$NH₂ wherein p is 1 to 5, —N(CH₂CH₂NH₂)₂, amidino, guanidino, aminosulfonyl, aminoalkoxy, aminoalkythio, lower acylamino, or benzyloxycarbonyl; and wherein the substituted aryl group is substituted with one more substituents, wherein each substituent is, independently, amino, halo, cyano, nitro, hydroxy, —NH (CH2)$_p$NH$_2$ wherein p is 1 to 5, —N(CH$_2$CH$_2$NH$_2$)$_2$, amidino, guanidino, aminosulfonyl, aminoalkoxy, aminoalkythio, lower acylamino, or benzyloxycarbonyl;

each NPL group is, independently, —B(OR$^4$)$_2$ or —(NR$^{3'}$)$_{q1NPL}$—U$^{NPL}$-LK$^{NPL}$-(NR$^{3''}$)$_{q2NPL}$—R$^{4'}$, wherein:

R$^3$, R$^{3'}$, and R$^{3''}$ are each, independently, hydrogen, alkyl, or alkoxy;

R$^4$ and R$^{4'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substituents, wherein each substituent is, independently, alkyl, halo, or haloalkyl;

each U$^{NPL}$ is, independently, absent or O, S, S(=O), S(=O)2, NR$^3$, —C(=O)—, —C(=O)—NR$^3$—, —C(=O)—N=N—NR$^3$—, —C(=O)—NR$^3$—N=N—, —N=N—NR$^3$—, —C(=N—N(R$^3$)$_2$)—, —C(=NR)—, —C(=O)O—, —C(=O)S—, —C(=S)—, —O—P(=O)2O—, —S—C=N—, or —C(=O)—NR$^3$—O—, wherein groups with two chemically nonequivalent termini can adopt both possible orientations;

each LK$^{NPL}$ is, independently, —(CH$_2$)$_{pNPL}$— or C$_{2-8}$alkenylenyl, wherein each of the —(CH$_2$)pNPL— or C$_{2-8}$alkenylenyl is optionally substituted with one or more substituents, wherein each substituent is, independently, amino, hydroxyl, aminoalkyl, hydroxylalkyl, or alkyl;

each pNPL is, independently, an integer from zero to 8;

q1NPL and q2NPL are each, independently, zero, 1, or 2;

each PL group is, independently, halo, hydroxyethoxymethyl, methoxyethoxymethyl, polyoxyethylene, or —(NR$^{5'}$)$_{q1PL}$—U$^{PL}$-LK$^{PL}$-(NR$^{5''}$)q2pL-V, wherein:

R$^5$, R$^{5'}$, and R$^{5''}$ are each, independently, hydrogen, alkyl, or alkoxy;

each U$^{PL}$ is, independently, absent or O, S, S(=O), S(=O)$_2$, NR$^5$, —C(=O)—, —C(=O)—NR$^5$—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —S—C=N—, or —C(=O)—NR$^5$—O—, wherein groups with two chemically nonequivalent termini can adopt either of the two possible orientations;

each R$^e$ is, independently, C$_{1-6}$alkyl, C$_{1-6}$haloalkyl, C$_{2-6}$alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more subsitutents, wherein each substituent is, independently, OH, amino, halo, C$_{1-6}$alkyl, C$_{1-6}$haloalkyl, aryl, arylalkyl, heteroaryl, heteroarylalkyl, cycloalkyl, or heterocycloalkyl;

R$^d$ and R$^e$ are, independently, H, C$_{1-6}$ alkyl, C$_{1-6}$ haloalkyl, C$_{2-6}$alkenyl, C$_{2-6}$alkynyl, aryl, heteroaryl, cycloalkyl, heterocycloalkyl, arylalkyl, heteroarylalkyl, cycloalkylalkyl, or heterocycloalkylalkyl, wherein each of the C$_{1-6}$alkyl, C$_{1-6}$ haloalkyl, C$_{2-6}$alkenyl, C$_{2-6}$alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, C$_{1-6}$alkyl, C$_{1-6}$haloalkyl, C$_{1-6}$haloalkyl, aryl, arylalkyl, heteroaryl, heteroarylalkyl, cycloalkyl, or heterocycloalkyl;

or R$^d$ and R$^e$ together with the N atom to which they are attached form a 4-, 5-, 6-, 7-, or 8-membered heterocycloalkyl;

each LK$^{PL}$ is, independently, —(CH$_2$)$_{pPL}$— or C$_{2-8}$alkenylenyl, wherein each of the —(CH2)$_{pPL}$— and C$_{2-8}$alkenylenyl is optionally substituted with one or more substituents, wherein each substituent is, independently, amino, hydroxyl, aminoalkyl, hydroxylalkyl, or alkyl;

each pPL is, independently, an integer from zero to 8;

q1PL and q2PL are each, independently, zero, 1, or 2;

m13 is an integer from 1 to about 10; and m14 is an integer from 1 to about 10.

The inhibitor of the anti-coagulation effect of heparin may, for example, be a compound of Formula IV, or pharmaceutically acceptable salt thereof, further in which:

each moiety of —[—X-A$_1$-Y—X-A$_2$-Y—]— is, independently, a moiety of:

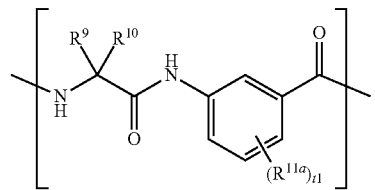

each R$^9$ is, independently, H, a PL group, or an NPL group;

each R$^{10}$ is, independently, H, a PL group, or an NPL group;

each R$^{11a}$ is, independently, a PL group or an NPL group; and each t1 is independently zero, 1, or 2.

The inhibitor of the anti-coagulation activity of heparin may, for example, be a compound of Formula V or a pharmaceutically acceptable salt thereof, as follows:

$$R^1—[—X-A^1-X—Y-A^2-Y—]_m—R^2 \quad V$$

or a pharmaceutically acceptable salt thereof, wherein:

each of the moiety of —X-A$^1$-X— is, independently, a moiety of Formula XXI-1, XXI-2, XXI-3, XXI-4, XXI-5, XXI-6, XXI-7, or XXI-8:

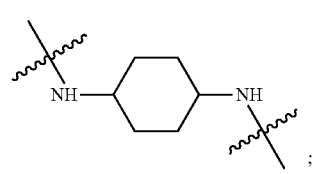

XXI-1

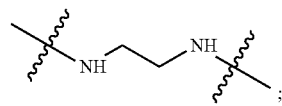

XXI-2

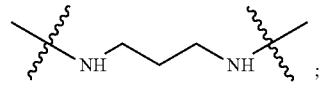

XXI-3

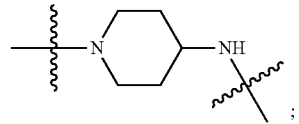

XXI-4

XXI-5
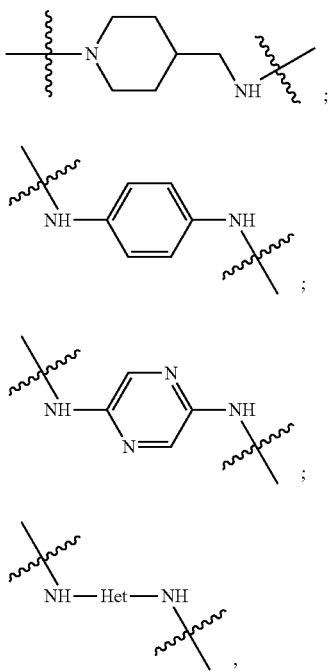

XXI-6

XXI-7

XXI-8 where Het is any 5 or 6-member ring heterocycle;
each of the moiety of —Y-A²-Y— is, independently, a moiety of Formula XXII-1, XXII-2, XXII-3, XXII-4, or XXII-5:

XXII-1
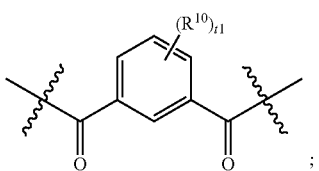

XXII-2
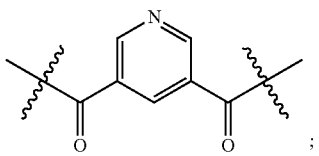

XXII-3
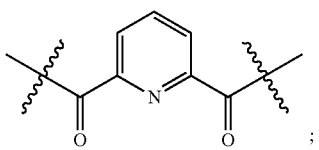

XXII-4
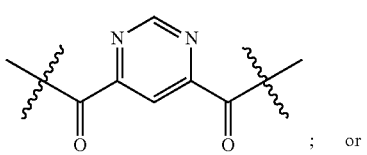 ; or

XXII-5
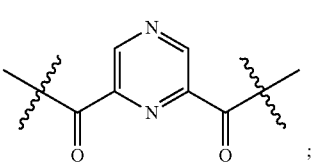

$R^1$ is hydrogen, —C(=O)$R^{11}$, or —Y-A²-Y—$R^{12}$;
$R^2$ is —OH, —NH$_2$, —NH(C$_{1-4}$ alkyl), —N(C$_{1-4}$ alkyl)2, —NH—C(NH)NH$_2$, —NH(CH$_2$)$_p$NH$_2$ wherein p is an integer from 1 to 5, —NH(CH$_2$)$_p$NH(C$_{1-4}$ alkyl) wherein p is an integer from 1 to 5, —NH(CH$_2$)$_p$N(C$_{1-4}$ alkyl)$_2$ wherein p is an integer from 1 to 5, —NH(CH$_2$)$_p$ NHC(=NH)NH$_2$ wherein p is an integer from 1 to 5, $R^{12a}$, or —X-A¹-X—$R^{13}$;
each $R^{10}$ is, independently, —C(=O)NH$_2$, —C(=O)NH(CH$_2$)$_p$NH$_2$ wherein p is an integer from 1 to 5, —C(=O)NH(CH2)$_p$NH(C$_{1-4}$ alkyl) wherein p is an integer from 1 to 5, —C(=O)NH(CH$_2$)$_p$N(C$_{1-4}$ alkyl)$_2$ wherein p is an integer from 1 to 5, —C(=O)NH(CH$_2$)$_p$ NHC(=NH)NH$_2$ wherein p is an integer from 1 to 5, —OCH$_3$, or —$R^{10a}$;
each $R^{10a}$ is, independently, C$_{1-8}$ alkyl substituted with $R^A$;
each $R^A$ is independently —NH$_2$, —NH(C$_{1-4}$ alkyl), —N(C$_{1-4}$ alkyl)$_2$, —NH—C(NH)NH$_2$, —C(=O)NH$_2$, or —C(=O)OH;
each $R^{11}$ is, independently, C$_{1-8}$ alkyl or aryl, each substituted with 0, 1, 2, or 3 substituents each independently selected from —OCH$_3$, —OR$^{11a}$, —C(=O)NH$_2$, —C(=O)NH(CH$_2$)$_p$NH$_2$ wherein p is an integer from 1 to 5, —C(=O)NH(CH$_2$)$_p$NH(C$_{1-4}$alkyl) wherein p is an integer from 1 to 5, —C(=O)NH(CH2)$_p$ N(C$_{1-4}$alkyl)$_2$ wherein p is an integer 20 from 1 to 5, —C(=O)NH(CH$_2$)$_p$NHC(=NH)NH$_2$ wherein p is an integer from 1 to 5, —NH$_2$, —NH(C$_{1-4}$ alkyl), —N(C$_{1-4}$ alkyl)$_2$, or —NH—C(=NH)NH$_2$;
each $R^{11a}$ is, independently, C$_{1-8}$ alkyl substituted with $R^B$;
each $R^B$ is, independently, —NH2, —NH(C$_{1-4}$ alkyl), —N(C$_{1-4}$ alkyl)$_2$, —NH—C(=NH)NH$_2$, or —C(=O)NH$_2$;
$R^{12}$ is —OH, —NH$_2$, —NH(C$_{1-4}$ alkyl), —N(C$_{1-4}$ alkyl)$_2$, —NH—C(NH)NH$_2$, —NH(CH$_2$)$_p$NH$_2$ wherein p is an integer from 1 to 5, —NH(CH$_2$)$_p$NH(C$_{1-4}$alkyl) wherein p is an integer from 1 to 5, —NH(CH$_2$)$_p$N(C$_{1-4}$ alkyl)$_2$ wherein p is an integer from 1 to 5, —NH(CH$_2$)$_p$ NHC(=NH)NH$_2$ wherein p is an integer from 1 to 5, or $R^{12a}$;
$R^{12a}$ is a moiety of Formula XXXI:

XXXI
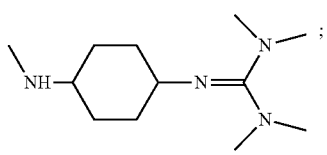

$R^{13}$ is hydrogen or —C(=O)$R^{11}$
t1 is zero, 1, or 2; and
m is 1, 2, 3, or 4, provided that:
(a) the compound of Formula V, or pharmaceutically acceptable salt thereof, comprises at least one moiety of Formula XXI-4;

(b) the compound of Formula V, or pharmaceutically acceptable salt thereof, comprises at least one moiety of Formula XXI-5;

(c) the compound of Formula V, or pharmaceutically acceptable salt thereof, comprises at least two different moieties of Formulas XXI-1, XXI-2, XXI-3, XXI-4, or XXI-5;

(d) the compound of Formula V, or pharmaceutically acceptable salt thereof, comprises at least one moiety of Formula XXI-4 and at least one moiety of Formula XXI-1, XX1-2, XX1-3, or XX1-5;

(e) the compound of Formula V, or pharmaceutically acceptable salt thereof, comprises at least one moiety of Formula XXI-5 and at least one moiety of Formula XXI-1, XXI-3, or XXI-4;

(f) the compound of Formula V, or pharmaceutically acceptable salt thereof, comprises at least one moiety of Formula XXII-2;

(g) the compound of Formula V, or pharmaceutically acceptable salt thereof, comprises at least one moiety of Formula XXII-3;

(h) the compound of Formula V, or pharmaceutically acceptable salt thereof, comprises at least one moiety of Formula XXII-2 and at least one moiety of Formula XXII-1, XXII-3, or XXII-4;

(i) the compound of Formula V, or pharmaceutically acceptable salt thereof, comprises at least one moiety of Formula XXII-3 and at least one moiety of Formula XXII-1, XXII-2, or XXII-4;

(j) the compound of Formula V, or pharmaceutically acceptable salt thereof, comprises at least two different moieties of Formulas XXII-1, XXII-2, XXII-3 and XXII-4;

(k) the compound of Formula V, or pharmaceutically acceptable salt thereof, comprises at least one moiety of Formula XXXI;

(l) the compound of Formula V, or pharmaceutically acceptable salt thereof, comprises at least two different moieties of Formula XXI-6, XXI-7, or XXI-8;

(m) the compound of Formula V, or pharmaceutically acceptable salt thereof, comprises at least one moiety of Formula XXI-6 and at least one moiety of Formula XXI-7 or XXI-8;

(n) the compound of Formula V, or pharmaceutically acceptable salt thereof, comprises at least one moiety of Formula XXI-7 and at least one moiety of Formula XXI-8;

(o) the compound of Formula V, or pharmaceutically acceptable salt thereof, comprises at least one moiety of Formula XXII-5;

(p) the compound of Formula V, or pharmaceutically acceptable salt thereof, comprises at least one moiety of Formula XXII-5 and at least one moiety of Formula XXII-1, XXII-3, or XXII-4;

(q) the compound of Formula V, or pharmaceutically acceptable salt thereof, comprises at least two different moieties of Formulas XXII-1, XXII-2, XXII-3, XXII-4, and XXII-5; or (r) the compound of Formula V, or pharmaceutically acceptable salt thereof, comprises at least one moiety of Formula XXXI, or a compound selected from Compound Nos. 201-427 of U.S. Pub. No. 2011/0178104 A1.

The inhibitor of the anti-coagulation activity of heparin may, for example, be a compound of Formula V, or pharmaceutically acceptable salt thereof, further in which the moiety of Formula XXII-1 is a moiety of XXII-1-a or XXII-1-b:

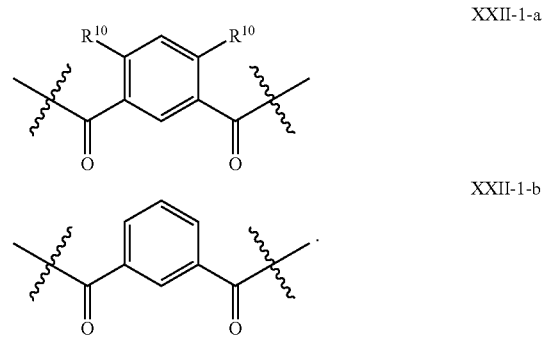

Methods for making compounds of Formulas I, II, IIa, III, IV or V are known in the art and disclosed in U.S. Pub. No. 2011/0178104 A1, U.S. Pub. No. 2006/0041023 A1, U.S. Pat. No. 7,173,102, and International Pub. No. WO2005/123660.

The inhibitor of the anticoagulation activity of heparin may, for example, be a compound or salt that binds to heparin with an $EC_{50}$ of less than about 100, 90, 80, 70, 60, 50, 40, 30, 20, 15, 10, 5, 2, 1, 0.9, 0.8, 0.7, 0.6, 0.5, 0.4, 0.3, 0.2, 0.1, 0.09, 0.08, 0.07, 0.06, 0.05, 0.02, 0.01, 0.001, 0.0001, or 0.00001 µg/mL. The inhibitor of the anticoagulation activity of heparin may, for example, be compound or salt that binds to heparin with an $EC_{50}$ less than about 30, 20, 15, 10, 5, 2, 1, 0.9, 0.8, 0.7, 0.6, 0.5, 0.4, 0.3, 0.2, 0.1, 0.01, 0.001, 0.0001, or 0.00001 µg/mL.

It has been reported that tetra-[5-(L)-lysyl-amino-O-methylsalicylamide] in a clinical study for the reversal of heparin anticoagulation therapy caused an undesirable decrease in blood pressure at the doses used. Tetra-[5-(L)-lysyl-amino-O-methylsalicylamide] is reported to bind heparin tightly and essentially irreversibly under physiological conditions. Advantageously, in the present invention, tetra-[5-(L)-lysyl-amino-O-methylsalicylamide] in a pre-bound-to-heparin form may be used for administration to the subject, which is believed to be free of the blood pressure decrease phenomena. Further advantageously, while heparin reversal in the context of anticoagulation therapy is often an acute situation in which slow administration is an unacceptable option for reducing side effects, in the present invention which is directed to the inhibition of metastasis, slow/slower administration (than used for acute reversal of heparin anticoagulation) is a valid option for reducing or eliminating side effects otherwise seen with acute administration of an inhibitor of the anticoagulation activity of heparin.

While vitamin K is not believed to be a direct inhibitor of the anticoagulation activity of heparin, it may nevertheless be used in any of the aforementioned embodiments, in combination with heparin, since it acts to compensate deficiencies in coagulation that may be subclinical or not clinically relevant outside the context of the administration of heparin but potentially deleterious during the administration of the heparin. In this regard, the co-administration of vitamin K at least in part counterbalances the anticoagulation effect of the heparin on a systemic level. Vitamin K may, for example, be used in addition to an inhibitor of the anticoagulation effect of heparin as described herein.

Vitamin K may, for example, be administered in a dose of 0.25-10.0 mg. This dose may be optionally repeated as needed, for example, every 2, 3, 4, 5, 6, or 7 days during the course of co-treatment with the heparin. Vitamin K may, for example, be administered orally, subcutaneously, intramuscularly or intravenously. Vitamin K used may, for example, be Vitamin $K_1$ or Vitamin $K_2$ or any mixture thereof. Synthetic forms of Vitamin K, such as $K_3$, $K_4$ and $K_5$ may also be employed.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, un-recited elements or method steps. However, wherever such open-ended language is recited herein, it is also meant to not only encompass but to also disclose the corresponding, more limited situations typically expressed as "consisting essentially of" and closed-ended language "consisting of."

As used herein, the terms "a" or "an" means "at least one" or "one or more" unless the context clearly indicates otherwise. However, wherever the term "a" or "an" is recited herein, it is also meant to not only encompass but to also disclose the corresponding, more limited instance of only one thing.

As used herein, the term "about" means that the numerical value is approximate and small variations would not significantly affect the practice of the disclosed embodiments. Where a numerical limitation is used, unless indicated otherwise by the context, "about" means the numerical value can vary by +10% and remain within the scope of the disclosed embodiments.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the term "alkyl" refers to a saturated hydrocarbon group which is straight-chained or branched. An alkyl group can contain from 1 to 20, from 2 to 20, from 1 to 10, from 1 to 8, from 1 to 6, from 1 to 4, or from 1 to 3 carbon atoms. Examples of alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

As used herein, the term "alkylene" or "alkylenyl" refers to a divalent alkyl linking group. An example of an alkylene (or alkylenyl) is methylene or methylenyl (i.e., —$CH_2$—).

As used herein, the term "alkenyl" refers to an alkyl group having one or more double carbon-carbon bonds. Examples of alkenyl groups include, but are not limited to, ethenyl, propenyl, cyclohexenyl, and the like.

As used herein, the term "alkenylenyl" refers to a divalent linking alkenyl group.

As used herein, the term "alkynyl" refers to an alkyl group having one or more triple carbon-carbon bonds. Examples of alkynyl groups include, but are not limited to, ethynyl, propynyl, and the like.

As used herein, the term "alkynylenyl" refers to a divalent linking alkynyl group.

As used herein, the term "haloalkyl" refers to an alkyl group having one or more halogen substituents. Examples of haloalkyl groups include, but are not limited to, $CF_3$, $C_2F_5$, $CHF_2$, $CCl_3$, $CHCl_2$, $C_2Cl_5$, $CH_2CF_3$, and the like.

As used herein, the term "aryl" refers to monocyclic or polycyclic (e.g., having 2, 3 or 4 fused rings) aromatic hydrocarbons. In some embodiments, aryl groups have from 6 to about 20 carbon atoms. In some embodiments, aryl groups have from 6 to 10 carbon atoms. Examples of aryl groups include, but are not limited to, phenyl, naphthyl, anthracenyl, phenanthrenyl, indanyl, indenyl, and the like.

As used herein, the term "cycloalkyl" refers to non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to about 15, from 3 to 10, from 3 to 8, from 3 to 6, from 4 to 6, from 3 to 5, or from 5 to 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl).

As used herein, the term "heteroaryl" refers to an aromatic heterocycle having up to 20 ring-forming atoms and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 1 to about 20 carbon atoms, from 1 to 5, from 1 to 4, from 1 to 3, or from 1 to 2, carbon atoms as ring-forming atoms. In some embodiments, the heteroaryl group contains 3 to 14, 3 to 7, or 5 to 6 ring-forming atoms. In some embodiments, the heteroaryl group has 1 to 4, 1 to 3, or 1 to 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like.

As used herein, the term "heterocycloalkyl" refers to non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Heterocycloalkyl groups can be mono or polycyclic (e.g., fused, bridged, or spiro systems). In some embodiments, the heterocycloalkyl group has from 1 to about 20 carbon atoms, or 3 to about 20 carbon atoms. In some embodiments, the heterocycloalkyl group contains 3 to 14, 3 to 7, or 5 to 6 ring-forming atoms. In some embodiments, the heterocycloalkyl group has 1 to 4, 1 to 3, or 1 to 2 heteroatoms. In some embodiments, the heterocycloalkyl group contains 0 to 3 double bonds. In some embodiments, the heterocycloalkyl group contains 0 to 2 triple bonds. Example of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (i.e., form a S(O) or S(O)$_2$). For another example, a ring-forming C atom can be substituted by oxo (i.e., form carbonyl). Also included in the definition of heterocycloalkyl are moieties that have one or more aromatic rings fused (i.e., having a bond in common with) to the nonaromatic heterocyclic ring including, but not limited to, pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "halo" refers to halogen groups including, but not limited to fluoro, chloro, bromo, and iodo.

As used herein, the term "alkoxy" refers to an —O-alkyl group. Examples of alkoxy groups include, but are not limited to, methoxy, ethoxy, propoxy (e.g., n-propoxy and isopropoxy), t-butoxy, and the like.

As used herein, the term "haloalkoxy" refers to an —O-haloalkyl group. An example of an haloalkoxy group is OCF$_3$.

As used herein, the term "alkylthio" refers to an —S-alkyl group. An example of an alkylthio group is —SCH$_2$CH$_3$.

As used herein, the term "arylalkyl" refers to a C$_1$-6 alkyl substituted by aryl and "cycloalkylalkyl" refers to C$_1$-6 alkyl substituted by cycloalkyl.

As used herein, the term "heteroarylalkyl" refers to a C$_1$-6 alkyl group substituted by a heteroaryl group, and "heterocycloalkylalkyl" refers to a C$_1$-6 alkyl substituted by heterocycloalkyl.

As used herein, the term "amino" refers to NH$_2$.

As used herein, the term "alkylamino" refers to an amino group substituted by an alkyl group. An example of an alkylamino is —NHCH$_2$CH$_3$.

As used herein, the term "arylamino" refers to an amino group substituted by an aryl group. An example of an alkylamino is —NH(phenyl).

As used herein, the term "aminoalkyl" refers to an alkyl group substituted by an amino group. An example of an aminoalkyl is —CH$_2$CH$_2$NH$_2$.

As used herein, the term "aminosulfonyl" refers to —S(=O)$_2$NH$_2$.

As used herein, the term "aminoalkoxy" refers to an alkoxy group substituted by an amino group. An example of an aminoalkoxy is —OCH$_2$CH$_2$NH$_2$.

As used herein, the term "aminoalkylthio" refers to an alkylthio group substituted by an amino group. An example of an aminoalkylthio is —SCH$_2$CH$_2$NH$_2$.

As used herein, the term "amidino" refers to —C(=NH)NH$_2$.

As used herein, the term "acylamino" refers to an amino group substituted by an acyl group (e.g., —O—C(=O)—H or —O—C(=O)-alkyl). An example of an acylamino is —NHC(=O)H or —NHC(=O)CH$_3$. The term "lower acylamino" refers to an amino group substituted by a loweracyl group (e.g., —O—C(=O)—H or —O—C(=O)—C$_1$-6 alkyl). An example of a lower acylamino is —NHC(=O)H or —NHC(=O)CH$_3$.

As used herein, the term "carbamoyl" refers to —C(=O)—NH$_2$.

As used herein, the term "cyano" refers to —CN.

As used herein, the term "dialkylamino" refers to an amino group substituted by two alkyl groups.

As used herein, the term "diazamino" refers to —N(NH$_2$)$_2$.

As used herein, the term "guanidino" refers to —NH(=NH)NH$_2$.

As used herein, the term "heteroarylamino" refers to an amino group substituted by a heteroaryl group. An example of an alkylamino is —NH-(2-pyridyl).

As used herein, the term "hydroxyalkyl" or "hydroxylalkyl" refers to an alkyl group substituted by a hydroxyl group. Examples of a hydroxylalkyl include, but are not limited to, —CH$_2$OH and —CH$_2$CH$_2$OH.

As used herein, the term "nitro" refers to —NO$_2$.

As used herein, the term "semicarbazone" refers to =NNHC(=O)NH$_2$.

As used herein, the term "ureido" refers to —NHC(=O)—NH$_2$.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound. For example, if a methyl group is optionally substituted, then 3 hydrogen atoms on the carbon atom may be replaced with substituent groups.

As used herein, the term, "compound" refers to all stereoisomers, tautomers, and isotopes of the compound described.

As used herein, the phrase "substantially isolated" refers to a compound that is at least partially or substantially separated from the environment in which it is formed or detected.

As used herein, the phrase "pharmaceutically acceptable" refers to those compounds, materials, compositions, and/or dosage forms which are, within the scope of sound medical judgment, suitable for use in contact with tissues of humans and animals, such as those known in the art.

As used herein, the term "subject" or "patient," used interchangeably, refers to any mammal, such as mice, rats, other rodents, rabbits, dogs, cats, swine, cattle, sheep, horses, or primates, such as humans.

Heparin used according to the invention may, for example, be unfractionated heparin or a low molecular weight heparin such as Tinzaparin, Reviparin, or Enoxaparin. Unfractionated heparin may, for example, be administered to achieve a plasma concentration of 0.05 to 1.0 units/mL, for example, 0.2 to 0.4 units/mL. The heparin may, for example, be dosed with an IV bolus dose of 5,000 to 10,000 units of heparin, followed by an infusion of 1,000 units per hour. The units are calculated in the same manner as if the heparin were to be used for anticoagulation even though the anticoagulation activity will be inhibited. In an alternative example, a loading dose of 50-100 units/kg of heparin followed by a constant infusion of 15-25 units/kg/hr may be used. Therapeutic levels for patients treated with heparin for venous thromboembolism are around 1 antifactor Xa unit/mL for low molecular weight heparins, typically measured at 3 to 4 hours after injection—for any heparins used according to the invention, a dosing providing the same plasma concentration of anti-factor Xa units, as would be present in the absence of inhibitors of heparin's anti-coagulation effect, may be used. Larger or smaller doses may also be used.

Doses of heparins such as unfractionated heparins or low molecular weight heparins used may, for example, be in the range of 0.1 mg-200 mg per day, such as 1 mg-200 mg per day, such as 1 mg-100 mg/day, such as 10 mg-100 mg per day, such as 20-80 mg, 30-70 mg or 30-60 mg per day. Dosing may continue, for example, for 2-7 days, for at least 7 days, for at least 10 days, for 10-14 days, for at least 14 days, for at least 20 days, for at least one month, or for at least two months. Dosing may be continuous and indefinite recognizing that there may be days that are skipped and/or that there may be on- and off-periods built into the dosing schedule. Continuous dosing is desirable to prevent an existing cancer susceptible to metastasis from spreading.

As described hereinabove, an amount of inhibitor of the anticoagulation effect of heparin may be used that at least substantially inhibits the anticoagulation activity of the amount of heparin used. For any particular heparin and such inhibitor, the relative amount of inhibitor to heparin required for complete or partial inhibition of the anticoagulation activity of the heparin may be determined empirically using anticoagulation assays such as those routine methods known in the art. For inhibitors of the anticoagulation activity of heparin that bind heparin, the relative amount of inhibitor to maximally "bind-up" the heparin can be routinely determined by titrating the binding to heparin (mixing known amounts of inhibitor and heparin under binding conditions and determining how much inhibitor remains unbound at different amounts). Heparin binding assays are well known in the art and disclosed, for example, in U.S. Pub. No. 2011/0178104 A1. For inhibitors of the anticoagulation activity of heparin that bind heparin, pharmaceutical compositions of the inhibitor bound to the heparin may, for example, be prepared by mixing an excess of the inhibitor with a quantity of the heparin under binding conditions and thereafter removing, for example by filtering, the unbound inhibitor from the mixture, prior to the administration to a patient.

While not wishing to be limited by any particular theory of mechanism, it is believed that heparins inhibit metastasis at least in part by modulating the interaction of otherwise metastasizing cells with selectins, particularly, P-selectin and L-selectin. The anti-metastatic moieties of heparin are distinct and/or separable from the anti-coagulant moieties. Anticoagulant activity of a heparin preparation can be depleted by passing the heparin through an antithrombin column. The heparin eluent maintains anti-metastatic activity but not substantial anti-coagulant activity. However, it is believed that the majority of the anti-metastatic heparin also has antithrombin binding sites and remains on the column. In contrast, the present invention can take advantage of essentially the entire anti-metastatic potential in a heparin population of glycosaminoglycans.

Each of the patents, patent applications or other publications cited herein is hereby incorporated by reference as if fully set forth in its entirety. Although the invention has been described in connection with various embodiments, it should be understood that the invention as claimed should not be unduly limited to such specific embodiments.

What is claimed is:

1. A method for preparing a pharmaceutical composition for the inhibition of metastasis in a mammal comprising the steps of:
   mixing in water or an aqueous solution
      an anti-metastatic heparin preparation having anti-coagulant activity in the absence of an inhibitor thereof, and
      an inhibitor of the anti-coagulation activity of heparin that binds heparin or a pharmaceutically-acceptable salt thereof, to obtain a solution in which at least some of the inhibitor of the anti-coagulation activity of heparin that binds heparin is bound to the anti-metastatic heparin preparation; and
   removing said inhibitor that remains unbound to the anti-metastatic heparin preparation from the anti-metastatic heparin preparation after the mixing step,
wherein the inhibitor of the anti-coagulation activity of heparin that binds heparin comprises a compound having the formula:

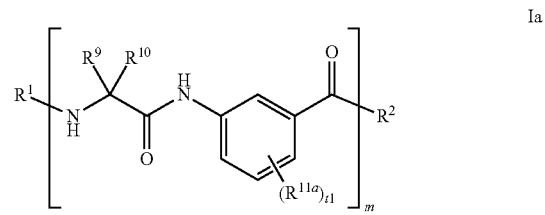

Ia or a pharmaceutically-acceptable salt thereof, wherein
   $R^1$ is hydrogen, an amino acid connected by its carbonyl group, $-C(=NR^3)-NR^{3''}R^{4'}$, $-C(=O)-(CH_2)_{pNPL}-R^{4'}$, $-C(=O)-(CH_2)_{pPL1}-V$, $-C(=O)-A_2-NH-C(=O)-(CH_2)_{pPL1}-V$, or $-C(=O)-A_2-NH-C(=O)-(CH_2)_{pNPL}-R^{4'}$;
   $R^3$ and $R^{3''}$ are each, independently, hydrogen, alkyl, or alkoxy;
   $R^{4'}$ is hydrogen, alkyl, alkenyl, alkynyl, cycloalkyl, aryl, or heteroaryl, each of which is optionally substituted with one or more substituents, wherein each substituent is, independently, alkyl, halo, or haloalkyl;
   each pNPL is, independently, an integer from 0 to 8;
   pPL1 is an integer from 1 to 5; and
   $A_2$ is optionally substituted arylene or optionally substituted heteroarylene, wherein $A_2$ is optionally substituted with one or more PL groups, one or more NPL groups, or a combination of one or more PL groups and one or more NPL groups;
   $R^2$ is OH, $OR^{600}$, $NH_2$, $NHR^{600}$, $N(R^{600})_2$, an amino acid connected by its amino group, an α amino acid amide connected by its α amino group, $-NH-(CH_2)_{pPL2}-V$, or $-NH-A_1-C(=O)-NH_2$;
   each $R^{600}$ is, independently, unsubstituted alkyl or aryl, or either alkyl or aryl substituted with OH, halo, cyan, nitro, amino, alkoxy, alkylthio, alkylamino, or dialkylamino;
   pPL2 is an integer from 1 to 5; and
   $A_1$ is optionally substituted arylene or optionally substituted heteroarylene, wherein $A_1$ is optionally substituted with one or more PL groups, one or more NPL groups, or a combination of one or more PL groups and one or more NPL groups;
   each $R^9$ is, independently, H, a PL group, or an NPL group;
   each $R^{10}$ is, independently, H, a PL group, or an NPL group;
   or $R^9$ and $R^{10}$, taken together, constitute the side chain of a D or L α amino acid;
   each $R^{11a}$ is, independently, a PL group or an NPL group;
   each NPL group is, independently, $-B(OR^{40})_2$ or $-(NR^{3'})_{q1NPL}-U^{NPL}-LK^{NPL}-(NR^{3''})_{q2NPL}-R^{40'}$;
   $R^{3'}$ is hydrogen, alkyl, or alkoxy;
   $R^{40}$ and $R^{40'}$ are each, independently, hydrogen, alkyl, alkenyl, alkynyl, cycloalkyl, aryl, or heteroaryl, wherein each of the alkyl, alkenyl, alkynyl, cycloalkyl, aryl, and heteroaryl is optionally substituted with one or more substituents, wherein each substituent is, independently, alkyl, halo, or haloalkyl;

each $U^{NPL}$ is, independently, absent or O, S, S(=O), S(=O)$_2$, NR$^3$, —(C=O)—, —C(=O)—NR$^3$—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —S—C=N—, or —C(=O)—NR$^3$—O—, wherein groups with two chemically nonequivalent termini can adopt both possible orientations;

each $LK^{NPL}$ is, independently, —(CH$_2$)$_{pNPL}$— or C$_{2-8}$ alkenylenyl, wherein each of the (CH$_2$)$_{pNPL}$ and C$_{2-8}$ alkenylenyl is optionally substituted with one or more substituents, wherein each substituent is, independently, amino, hydroxyl, aminoalkyl, hydroxylalkyl, or alkyl;

q1NPL and q2NPL are each, independently, 0, 1, or 2;

each PL group is, independently, halo, hydroxyethoxymethyl, methoxyethoxymethyl, polyoxyethylene, or —(NR$^{5'}$)$_{q1PL}$—U$^{PL}$-LK$^{PL}$-(NR$^{5''}$)$_{q2PL}$—V, wherein:

R$^{5'}$ and R$^{5''}$ are each, independently, hydrogen, alkyl, or alkoxy;

each $U^{PL}$ is, independently, absent or O, S, S(=O), S(=O)$_2$, NR$^5$, —C(=O)—, —C(=O)—NR$^5$—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —S—C=N—, or —C(=O)—NR$^5$—O—, wherein groups with two chemically nonequivalent termini can adopt either of the two possible orientations;

each V is, independently, nitro, cyano, amino, halo, hydroxy, alkoxy, alkylthio, alkylamino, dialkylamino, amido, alkylamido, dialkylamido, —NH(CH$_2$)$_p$NH$_2$ wherein p is 1 to 5, —C(=O)NH(CH$_2$)$_p$NH$_2$ wherein p is 1 to 5, —C(=O)NH(CH$_2$)$_p$NHC(=NH)NH$_2$ wherein p is 1 to 5, —C(=O)NH(CH$_2$)$_p$NHC(=O)NH$_2$ wherein p is 1 to 5, —NHC(=O)-alkyl, —N(CH$_2$CH$_2$NH$_2$)$_2$, diazamino, amidino, guanidino, ureido, carbamoyl, —C(=O)OH, —C(=O)OR$^e$, —C(=O)NH—OH, —O—NH—C(=NH)NH$_2$, —NH—S(=O)$_2$OH, —S(=O)$_2$OH, NR$^d$R$^e$, semicarbazone, aryl, cycloalkyl, heterocycloalkyl, or heteroaryl, wherein each of the aryl and cycloalkyl is substituted with one or more substituents, wherein each of the heterocycloalkyl and heteroaryl is optionally substituted with one or more substituents, and wherein each of the substituents for the aryl, cycloalkyl, heterocycloalkyl, and heteroaryl is, independently, nitro, cyano, amino, halo, hydroxy, alkoxy, alkylthio, alkylamino, dialkylamino, —NH(CH$_2$)$_p$NH$_2$ wherein p is 1 to 5, —N(CH$_2$CH$_2$NH$_2$)$_2$, diazamino, amidino, guanidino, ureido, carbamoyl, —C(=O)OH, —C(=O)OR$^e$, —C(=O)NH—OH, —O—NH—C(=NH)NH$_2$, —NH—S(=O)$_2$OH, S(=O)$_2$OH, NR$^d$R$^e$, semicarbazone, aminosulfonyl, aminoalkoxy, aminoalkythio, lower acylamino, or benzyloxycarbonyl;

each $R^c$ is, independently, C$_{1-6}$ alkyl, C$_{1-6}$ haloalkyl, C$_{2-6}$ alkenyl, C$_{2-6}$ alkynyl, aryl, cycloalkyl, heteroaryl, heterocycloalkyl, arylalkyl, heteroarylalkyl, cycloalkylalkyl, or heterocycloalkylalkyl, each optionally substituted by one or more substituents, wherein each substituent is, independently, OH, amino, halo, C$_{1-6}$ alkyl, C$_{1-6}$ haloalkyl, aryl, arylalkyl, heteroaryl, heteroarylalkyl, cycloalkyl, or heterocycloalkyl;

$R^d$ and $R^e$ are, independently, H, C$_{1-6}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl, or heterocycloalkylalkyl, wherein each of the C$_{1-6}$ alkyl, C$_{1-6}$ haloalkyl, C$_{2-6}$ alkenyl, C$_{2-6}$ alkynyl, aryl, heteroaryl, cycloalkyl, heterocycloalkyl, arylalkyl, heteroarylalkyl, cycloalkylalkyl and heterocycloalkylalkyl is optionally substituted by OH, amino, halo, C$_{1-6}$ alkyl, C$_{1-6}$ haloalkyl, C$_{1-6}$ haloalkyl, aryl, arylalkyl, heteroaryl, heteroarylalkyl, cycloalkyl, or heterocycloalkyl;

or $R^d$ and $R^e$ together with the N atom to which they are attached form a 4-, 5-, 6-, 7-, or 8-membered heterocycloalkyl;

each $LK^{PL}$ is, independently —(CH$_2$)$_{pPL3}$— or C$_{2-8}$ alkenylenyl, wherein each of the —(CH$_2$)$_{pPL3}$— or C$_{2-8}$ alkenylenyl is optionally substituted with one or more substituents, wherein each substituent is, independently, amino, hydroxyl, aminoalkyl, hydroxylalkyl, or alkyl;

each pPL3 is, independently, an integer from 0 to 8;

q1PL and q2PL are each, independently, 0, 1, or 2;

each t1 is, independently, 0, 1, or 2; and m is an integer from 1 to 20, and wherein the compound or pharmaceutically acceptable salt thereof binds the antithrombin III binding site of heparin.

2. The method of claim 1,
wherein in the mixing step, the quantity of the inhibitor of the anti-coagulation activity of heparin that binds heparin or a pharmaceutically-acceptable salt thereof is provided in excess of the anti-thrombin III binding sites present in the anti-metastatic heparin preparation having anti-coagulant activity in the absence of an inhibitor thereof that is provided.

3. The method of claim 1, wherein m is an integer from 3 to 6.

4. The method of claim 1, further comprising the step of:
after the removing step, drying the anti-metastatic heparin preparation to obtain a dry anti-metastatic heparin preparation to which at least some of the inhibitor of the anti-coagulation activity of heparin that binds heparin is bound.

5. The method of claim 1, wherein the inhibitor of the anti-coagulation activity of heparin that binds heparin comprises a compound having the formula:

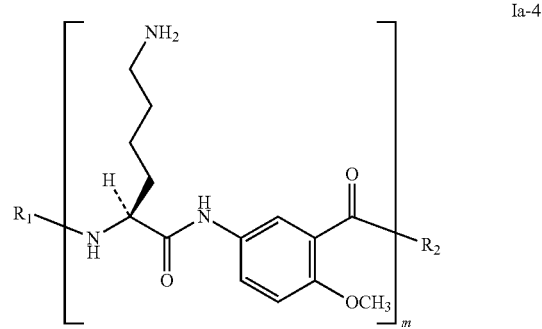

Ia-4 or a pharmaceutically acceptable salt thereof.

6. The method of claim 5, wherein m is an integer from 3 to 6.

7. The method of claim 5, further comprising the step of:
after the removing step, drying the anti-metastatic heparin preparation to obtain a dry anti-metastatic heparin preparation to which at least some of the inhibitor of the anti-coagulation activity of heparin that binds heparin is bound.

8. The method of claim 5, wherein the inhibitor of the anti-coagulation activity of heparin that binds heparin comprises a compound having the formula:

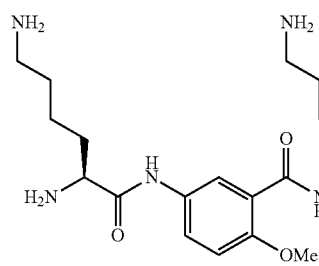
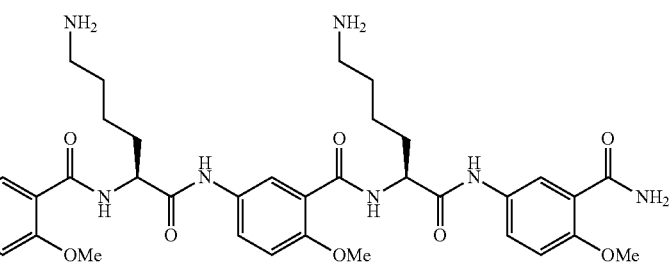
or a pharmaceutically acceptable salt thereof.
9. The method of claim 8, further comprising the step of: after the removing step, drying the anti-metastatic heparin preparation to obtain a dry anti-metastatic heparin preparation to which at least some of the inhibitor of the anti-coagulation activity of heparin that binds heparin is bound.
* * * * *